US010829294B2

(12) United States Patent
Sebastian et al.

(10) Patent No.: US 10,829,294 B2
(45) Date of Patent: Nov. 10, 2020

(54) AEROSOL PRECURSOR COMPOSITION MIXING SYSTEM FOR AN AEROSOL DELIVERY DEVICE

(71) Applicant: RAI Strategic Holdings, Inc., Winston-Salem, NC (US)

(72) Inventors: Andries Sebastian, Winston-Salem, NC (US); Percy Phillips, Pfafftown, NC (US); James Rogers, Cornelius, NC (US); Michael Davis, Clemmons, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 40 days.

(21) Appl. No.: 16/210,831

(22) Filed: Dec. 5, 2018

(65) Prior Publication Data

US 2019/0106268 A1 Apr. 11, 2019

Related U.S. Application Data

(63) Continuation of application No. 15/165,928, filed on May 26, 2016, now Pat. No. 10,179,690.

(51) Int. Cl.
*B65D 83/42* (2006.01)
*A61M 15/06* (2006.01)
(Continued)

(52) U.S. Cl.
CPC ............ *B65D 83/425* (2013.01); *A24B 15/16* (2013.01); *A24F 47/008* (2013.01);
(Continued)

(58) Field of Classification Search
CPC ........ B65D 83/42; B65D 83/425; A24B 15/16
(Continued)

(56) References Cited

U.S. PATENT DOCUMENTS 2,641,399 A * 7/1954 McBean ............... B65B 31/003
141/3
2,684,805 A 7/1954 McBean
(Continued)

FOREIGN PATENT DOCUMENTS

CN 204393355 6/2015
WO WO 00/24649 5/2000
(Continued)

OTHER PUBLICATIONS

Md Khaja Shareef, "Science Inspiration How does an Aerosol Spray Work?", http://scienceinspiration.blogspot.com/2012/05/how-does-aerosol-spray-work.html, May 29, 2012, pp. 1-4.
(Continued)

*Primary Examiner* — Timothy L Maust
(74) *Attorney, Agent, or Firm* — Womble Bond Dickinson (US) LLP

(57) ABSTRACT

The present disclosure relates to an aerosol delivery device filling system. The system includes multiple source containers each respectively including a differing aerosol precursor composition. The system further includes a mixing container configured to engage the source containers to receive and mix the aerosol precursor compositions to form a mixed aerosol precursor composition. An aerosol delivery device may engage the mixing container to receive at least a portion of the mixed aerosol precursor composition. A related method for customizing an aerosol precursor composition is also provided.

13 Claims, 18 Drawing Sheets

(51) Int. Cl.
*B65D 81/32* (2006.01)
*B65D 83/68* (2006.01)
*B65D 83/72* (2006.01)
*B01F 13/00* (2006.01)
*B01F 13/10* (2006.01)
*B01F 15/00* (2006.01)
*B01F 15/02* (2006.01)
*A61M 15/00* (2006.01)
*A24B 15/16* (2020.01)
*A24F 47/00* (2020.01)
*A61M 11/04* (2006.01)

(52) U.S. Cl.
CPC .......... *A61M 15/009* (2013.01); *A61M 15/06* (2013.01); *B01F 13/0022* (2013.01); *B01F 13/1072* (2013.01); *B01F 15/00512* (2013.01); *B01F 15/00889* (2013.01); *B01F 15/0238* (2013.01); *B65D 81/3211* (2013.01); *B65D 83/42* (2013.01); *B65D 83/682* (2013.01); *B65D 83/72* (2013.01); *A61M 11/042* (2014.02); *A61M 15/0003* (2014.02); *A61M 2209/045* (2013.01)

(58) Field of Classification Search
USPC .............. 141/20, 107, 302, 351; 222/145.5; 137/585, 625.4
See application file for complete search history.

(56) References Cited

U.S. PATENT DOCUMENTS

| | | | |
|---|---|---|---|
| 3,298,383 A | | 1/1967 | Cooper |
| 3,451,593 A | * | 6/1969 | Dillarstone ............. B05B 1/341 |
| | | | 222/130 |
| 3,459,245 A | | 8/1969 | Schreiber et al. |
| 3,575,319 A | * | 4/1971 | Safianoff .............. B29B 7/7438 |
| | | | 222/135 |
| 3,620,266 A | | 11/1971 | Ryder |
| 3,704,812 A | * | 12/1972 | Marand ................. B05B 7/2421 |
| | | | 222/136 |
| 3,713,464 A | | 1/1973 | Nigro |
| 4,141,470 A | | 2/1979 | Schulte et al. |
| 4,170,319 A | * | 10/1979 | Suh ....................... B29B 7/7404 |
| | | | 222/134 |
| 4,773,562 A | * | 9/1988 | Gueret ................... A45D 40/24 |
| | | | 222/135 |
| 4,801,046 A | * | 1/1989 | Miczka ................. B65D 83/38 |
| | | | 222/95 |
| 4,917,156 A | | 4/1990 | Varlet |
| 4,999,976 A | | 3/1991 | Smith |
| 5,345,980 A | | 9/1994 | Burt et al. |
| 5,588,472 A | | 12/1996 | Johnson |
| 5,899,362 A | * | 5/1999 | Moran ................ B01F 15/0429 |
| | | | 222/136 |
| 5,924,599 A | * | 7/1999 | Brown .................. B05B 7/2467 |
| | | | 222/135 |
| 6,116,296 A | | 9/2000 | Turunen |
| 6,691,746 B2 | | 2/2004 | Brennan et al. |
| 6,848,601 B2 | | 2/2005 | Greer, Jr. |
| 6,948,534 B1 | * | 9/2005 | Hirz ...................... B65B 31/003 |
| | | | 141/20 |
| 7,021,499 B2 | * | 4/2006 | Hansen .................. A47L 13/00 |
| | | | 222/135 |
| 7,264,024 B2 | * | 9/2007 | Funt ........................ F17C 13/04 |
| | | | 141/2 |
| 7,854,350 B2 | * | 12/2010 | Lasserre ................ B65D 83/68 |
| | | | 222/135 |
| 8,505,548 B2 | | 8/2013 | Hearn |
| 8,757,169 B2 | | 6/2014 | Gysland |
| 9,226,495 B2 | * | 1/2016 | Berentsveig .............. A61L 9/14 |
| 9,469,468 B2 | * | 10/2016 | Shibata .................. B65D 83/48 |
| 10,179,690 B2 | * | 1/2019 | Sebastian .......... B01F 15/00889 |
| 2003/0183651 A1 | | 10/2003 | Greer, Jr. |
| 2005/0268908 A1 | * | 12/2005 | Bonney ............. A61M 15/0045 |
| | | | 128/203.15 |
| 2008/0093469 A1 | | 4/2008 | Kline |
| 2015/0313280 A1 | | 11/2015 | Hearn |
| 2016/0120219 A1 | | 5/2016 | Vallar |
| 2017/0341851 A1 | | 11/2017 | Speck |

FOREIGN PATENT DOCUMENTS

| | | |
|---|---|---|
| WO | WO 2014/155089 | 10/2014 |
| WO | WO 2014/155090 | 10/2014 |
| WO | WO 2014/155092 | 10/2014 |
| WO | WO 2014/155095 | 10/2014 |
| WO | WO 2014/203063 | 12/2014 |
| WO | WO 2015/028815 | 3/2015 |
| WO | WO 2015/140555 | 9/2015 |
| WO | WO 2015/157224 | 10/2015 |

OTHER PUBLICATIONS

Ali Heibi, Joy Reactor, http://joyreactor.com/post/1311710, Retrieved from Internet May 26, 2016, pp. 1-6.
International Search Report dated Aug. 31, 2017 for International Application No. PCT/IB2017/052973.

* cited by examiner

```
┌─────────────────────────────────────────────┐
│   RECEIVE A FIRST AEROSOL PRECURSOR         │─── 802
│   COMPOSITION FROM A FIRST SOURCE CONTAINER │
└─────────────────────────────────────────────┘
                      │
                      ▼
┌─────────────────────────────────────────────┐
│ RECEIVE A SECOND AEROSOL PRECURSOR          │─── 804
│ COMPOSITION FROM A SECOND SOURCE CONTAINER, │
│ THE SECOND AEROSOL PRECURSOR COMPOSITION    │
│ DIFFERING FROM THE FIRST AEROSOL PRECURSOR  │
│ COMPOSITION                                 │
└─────────────────────────────────────────────┘
                      │
                      ▼
┌─────────────────────────────────────────────┐
│ MIX THE FIRST AEROSOL PRECURSOR COMPOSITION │─── 806
│ AND THE SECOND AEROSOL PRECURSOR            │
│ COMPOSITION IN A MIXING CONTAINER TO FORM   │
│ A MIXED AEROSOL PRECURSOR COMPOSITION       │
└─────────────────────────────────────────────┘
                      │
                      ▼
┌─────────────────────────────────────────────┐
│ DISPENSE THE MIXED AEROSOL PRECURSOR        │─── 808
│ COMPOSITION TO AN AEROSOL DELIVERY DEVICE   │
└─────────────────────────────────────────────┘
```

AEROSOL PRECURSOR COMPOSITION MIXING SYSTEM FOR AN AEROSOL DELIVERY DEVICE

CROSS-REFERENCE TO RELATED APPLICATIONS

This application is a divisional of U.S. application Ser. No. 15/165,928, filed May 26, 2016, which application is hereby incorporated by reference in its entirety in this application.

FIELD OF THE DISCLOSURE

The present disclosure relates to aerosol delivery devices, and more particularly, to accessories configured to mix an aerosol precursor composition for an aerosol delivery device. The aerosol delivery device may include an atomizer comprising a heating element configured to heat an aerosol precursor composition. The aerosol precursor composition, which may include components made or derived from tobacco or otherwise incorporate tobacco, is heated by the atomizer to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. App. Pub. Nos. 2014/0096781 to Sears et al., 2014/0283859 to Minskoff et al., 2015/0335070 to Sears et al., 2015/0335071 to Brinkley et al., 2016/0007651 to Ampolini et al., and 2016/0050975 to Worm et al.; all of which are incorporated herein by reference.

As noted above, aerosol delivery devices may heat an aerosol precursor composition to produce an aerosol. In some embodiments aerosol delivery devices may be refillable. Thereby, a user may select a desired type of aerosol precursor composition for usage therein. However, numerous types of aerosol precursor compositions may be available. Accordingly, a user seeking a specific type of aerosol precursor composition may have the aerosol precursor composition mixed at a specialty shop. However, acquiring a customized aerosol precursor composition may be costly and/or inconvenient. Thus, it may be desirable to provide aerosol delivery devices with accessories configured to produce customized aerosol precursor compositions.

BRIEF SUMMARY OF THE DISCLOSURE

The present disclosure relates to aerosol delivery devices which, in certain embodiments, may be characterized as electronic cigarettes. More particularly, the present disclosure relates to accessories that may be used in conjunction with an aerosol delivery device to refill the aerosol delivery device with a custom-mixed aerosol precursor composition.

In one aspect an aerosol precursor composition mixing system is provided. The system may include a source container configured to contain an aerosol precursor composition and defining a source container outlet. A source container outlet valve may be coupled to the source container outlet. The system may additionally include a mixing container defining a mixing container inlet and a mixing container outlet. A mixing container inlet valve may be coupled to the mixing container inlet and a mixing container outlet valve may be coupled to the mixing container outlet. The source container outlet valve and the mixing container inlet valve may be configured to engage one another and open during engagement to allow transfer of the aerosol precursor composition from the source container to the mixing container. The mixing container outlet valve may be configured to open during engagement with an aerosol delivery device.

In some embodiments at least one of the source container outlet valve, the mixing container inlet valve, and the mixing container outlet valve may include a one-way valve. The one-way valve may include a spring configured to bias the one-way valve to a closed configuration. The source container may further include a pressurized propellant. The source container may include a pump mechanism configured to pump the aerosol precursor composition into the mixing container. The source container outlet valve may at least partially extend out of the source container and the mixing container inlet valve may be at least partially recessed within the mixing container. The source container outlet valve may include an extension and the mixing container inlet valve may include a receptacle. The source container may include one or more surface features at an internal surface thereof.

In an additional aspect an aerosol delivery device filling system is provided. The system may include a first source container including a first aerosol precursor composition. Further, the system may include a second source container including a second aerosol precursor composition differing from the first aerosol precursor composition. The system may additionally include a mixing container configured to engage the first source container to receive at least a portion of the first aerosol precursor composition and engage the second source container to receive at least a portion of the second aerosol precursor composition to form a mixed aerosol precursor composition. The system may further include an aerosol delivery device configured to engage the mixing container to receive at least a portion of the mixed aerosol precursor composition.

In some embodiments at least one of the first source container and the second source container may further include a pressurized propellant. At least one of the first source container and the second source container may include a pump mechanism configured to pump the aerosol precursor composition into the mixing container. The first source container and the second source container may respectively define a source container outlet and include a source container outlet valve coupled to the source container outlet. The mixing container may define a mixing container inlet and a mixing container outlet and may include a mixing container inlet valve coupled to the mixing container inlet and a mixing container outlet valve coupled to the mixing container outlet. The source container outlet valve of the first source container and the mixing container inlet valve may be configured to engage one another and open during engagement to allow transfer of the aerosol precursor composition from the first source container to the mixing container. The source container outlet valve of the second source container and the mixing container inlet valve may be configured to engage one another and open during engagement to allow transfer of the aerosol precursor composition from the second source container to the mixing container. The mixing container outlet valve may be configured to open during engagement with the aerosol delivery device. At least one of the source container outlet valve, the mixing container inlet valve, and the mixing container outlet valve may include a one-way valve. The one-way valve may include a spring configured to bias the one-way valve to a closed configuration.

In an additional aspect a method for customizing an aerosol precursor composition is provided. The method may include receiving a first aerosol precursor composition from a first source container. Further, the method may include receiving a second aerosol precursor composition from a second source container, the second aerosol precursor composition differing from the first aerosol precursor composition. The method may additionally include mixing the first aerosol precursor composition and the second aerosol precursor composition in a mixing container to form a mixed aerosol precursor composition. The method may further include dispensing the mixed aerosol precursor composition to an aerosol delivery device.

In some embodiments receiving the first aerosol precursor composition from the first source container may include opening a first source container outlet valve and a mixing container inlet valve. Receiving the second aerosol precursor composition from the second source container may include opening a second source container outlet valve and the mixing container inlet valve. Opening the first source container outlet valve and the mixing container inlet valve may include engaging the first source container outlet valve with the mixing container inlet valve. Opening the second source container outlet valve and the mixing container inlet valve may include engaging the second source container outlet valve with the mixing container inlet valve. The method may further include closing the first source container outlet valve and the mixing container inlet valve during disengagement thereof. Additionally, the method may include closing the second source container outlet valve and the mixing container inlet valve during disengagement thereof. Dispensing the mixed aerosol precursor composition to the aerosol delivery device may include opening a mixing container outlet valve. The method may further include closing the mixing container outlet valve during disengagement from the aerosol delivery device.

These and other features, aspects, and advantages of the disclosure will be apparent from a reading of the following detailed description together with the accompanying drawings, which are briefly described below.

BRIEF DESCRIPTION OF THE FIGURES

Figure 1:
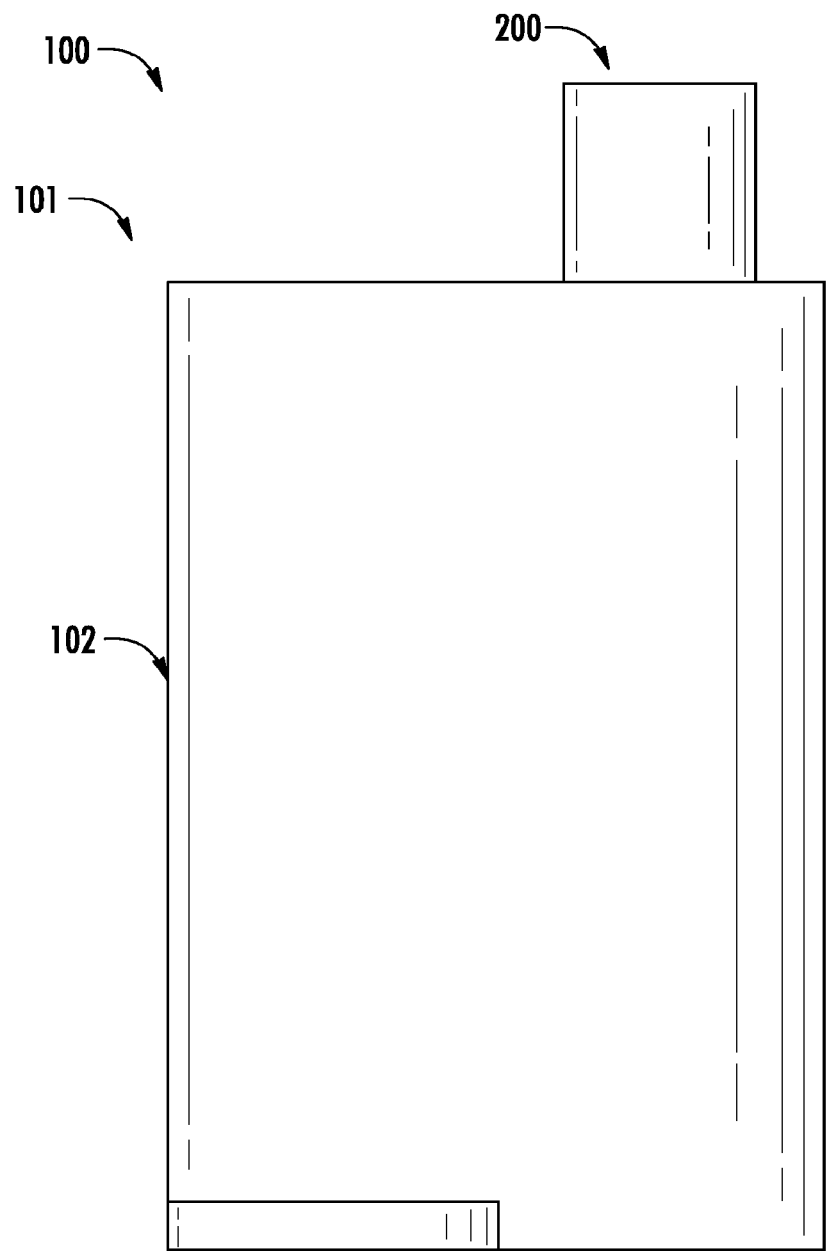
Figure 2:
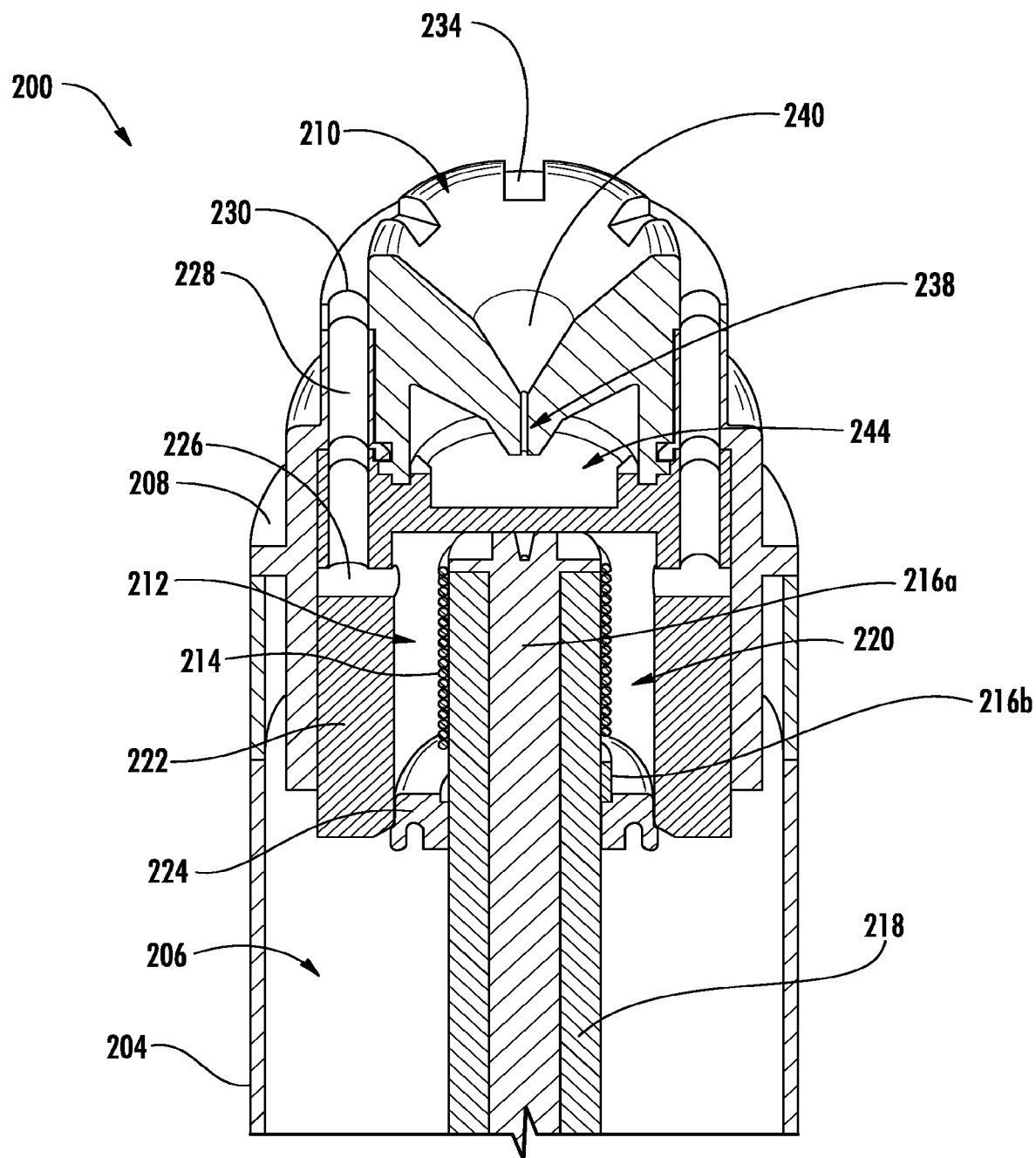
Figure 3:
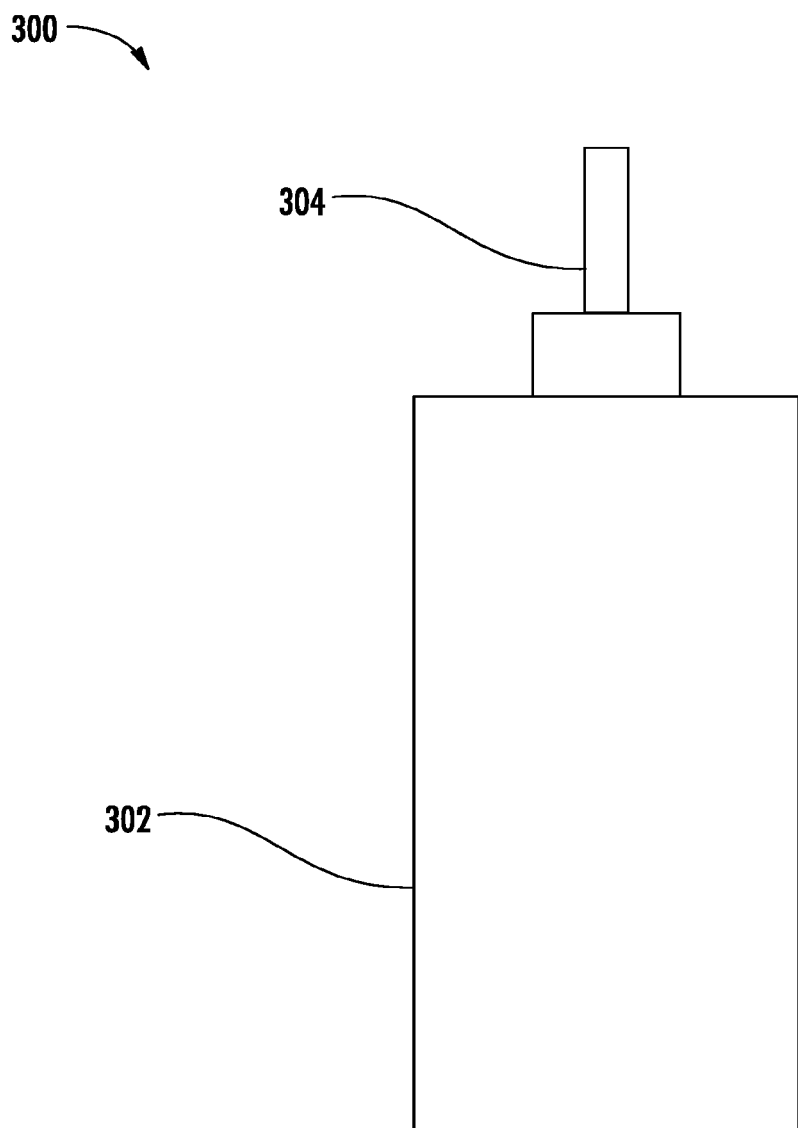
Figure 4:
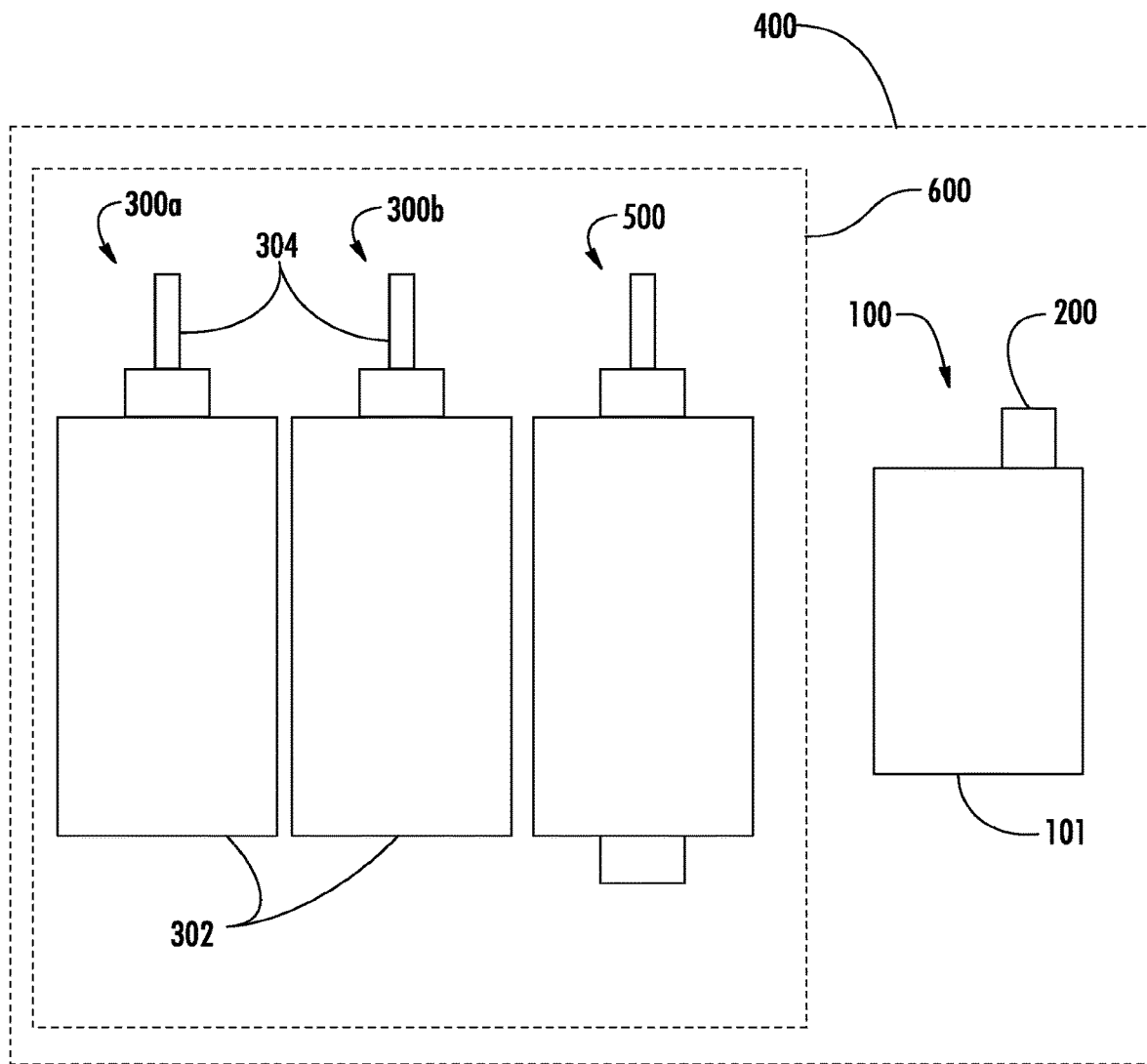
Figure 5:
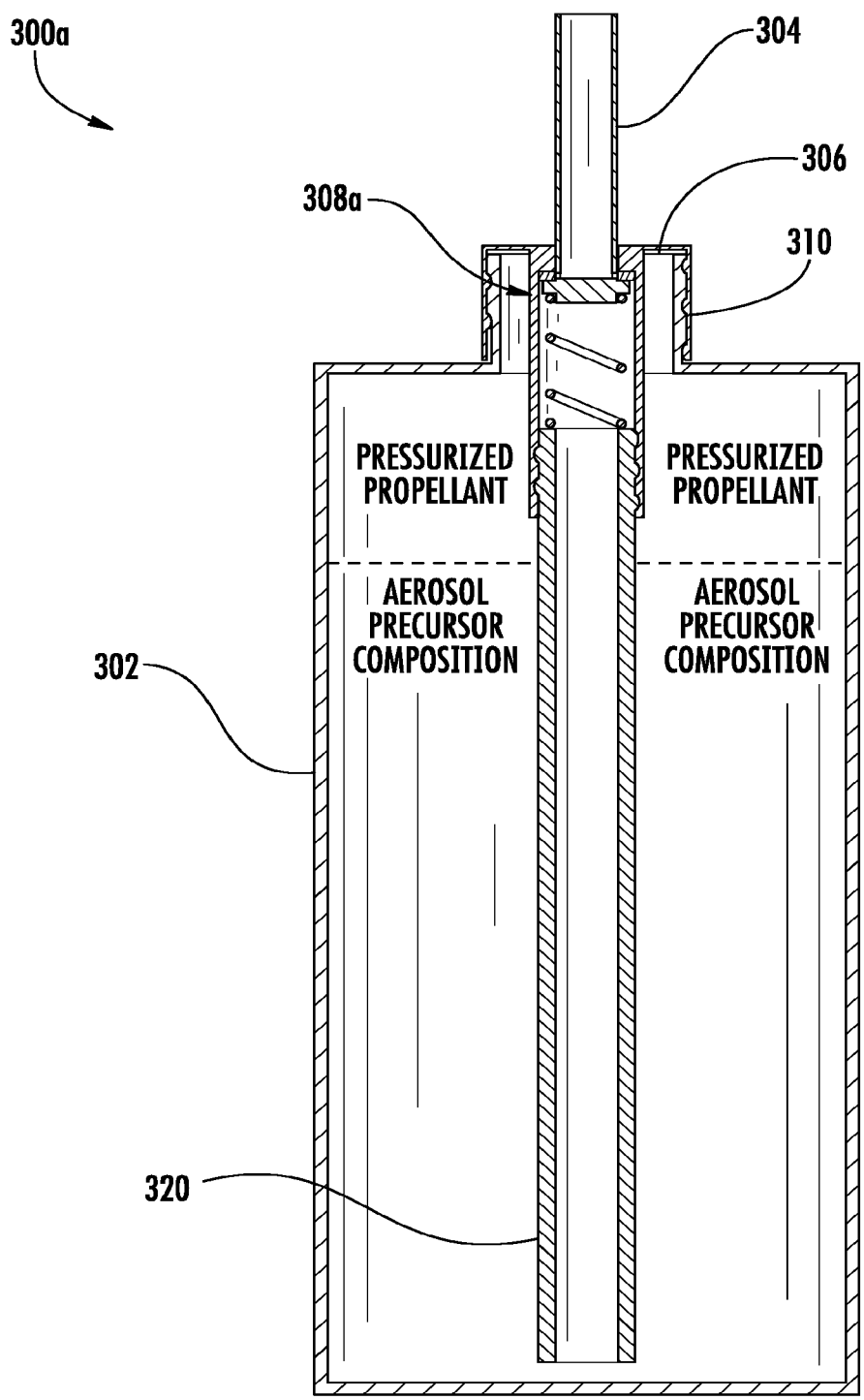
Figure 6:
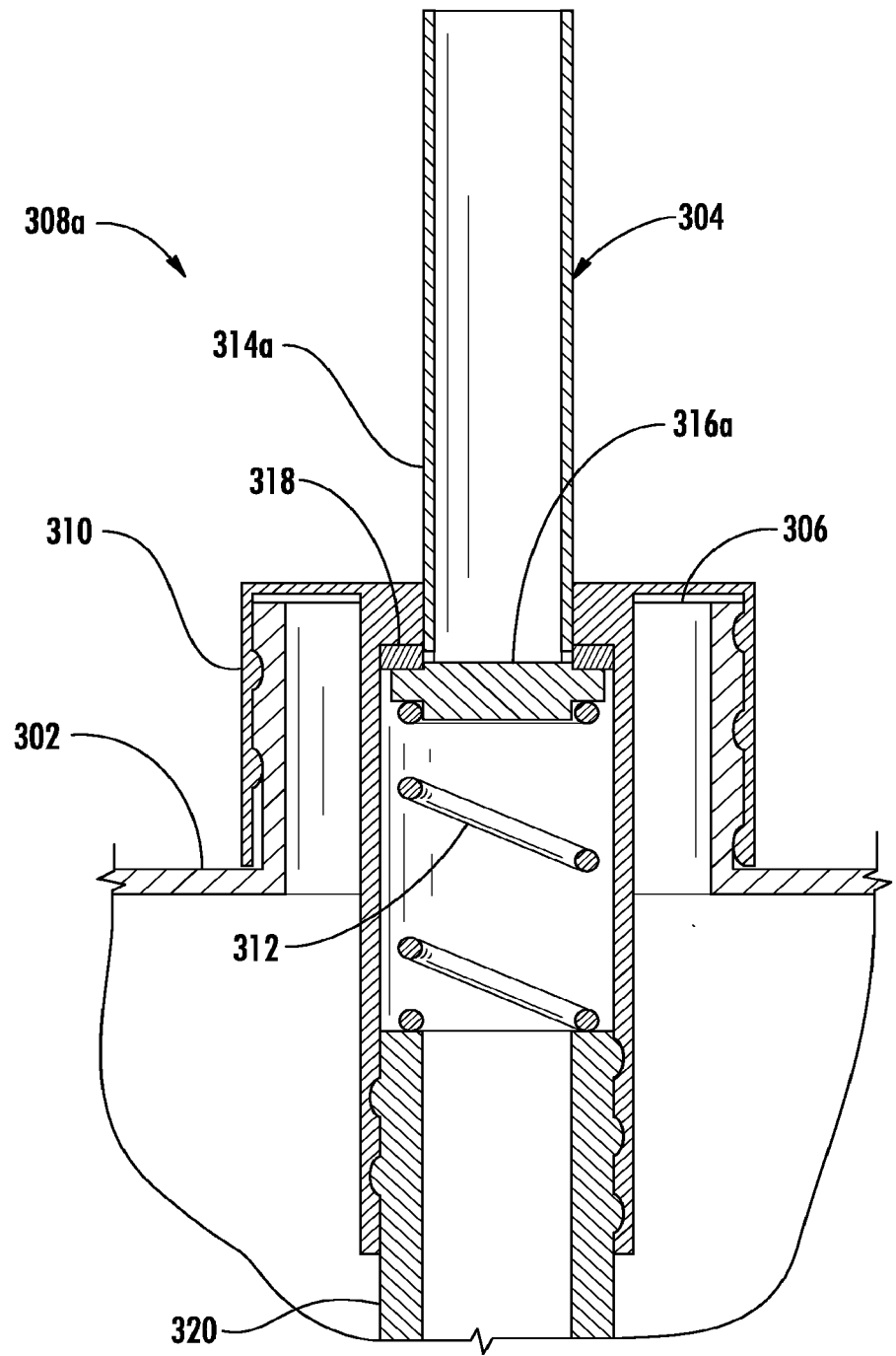
Figure 7:
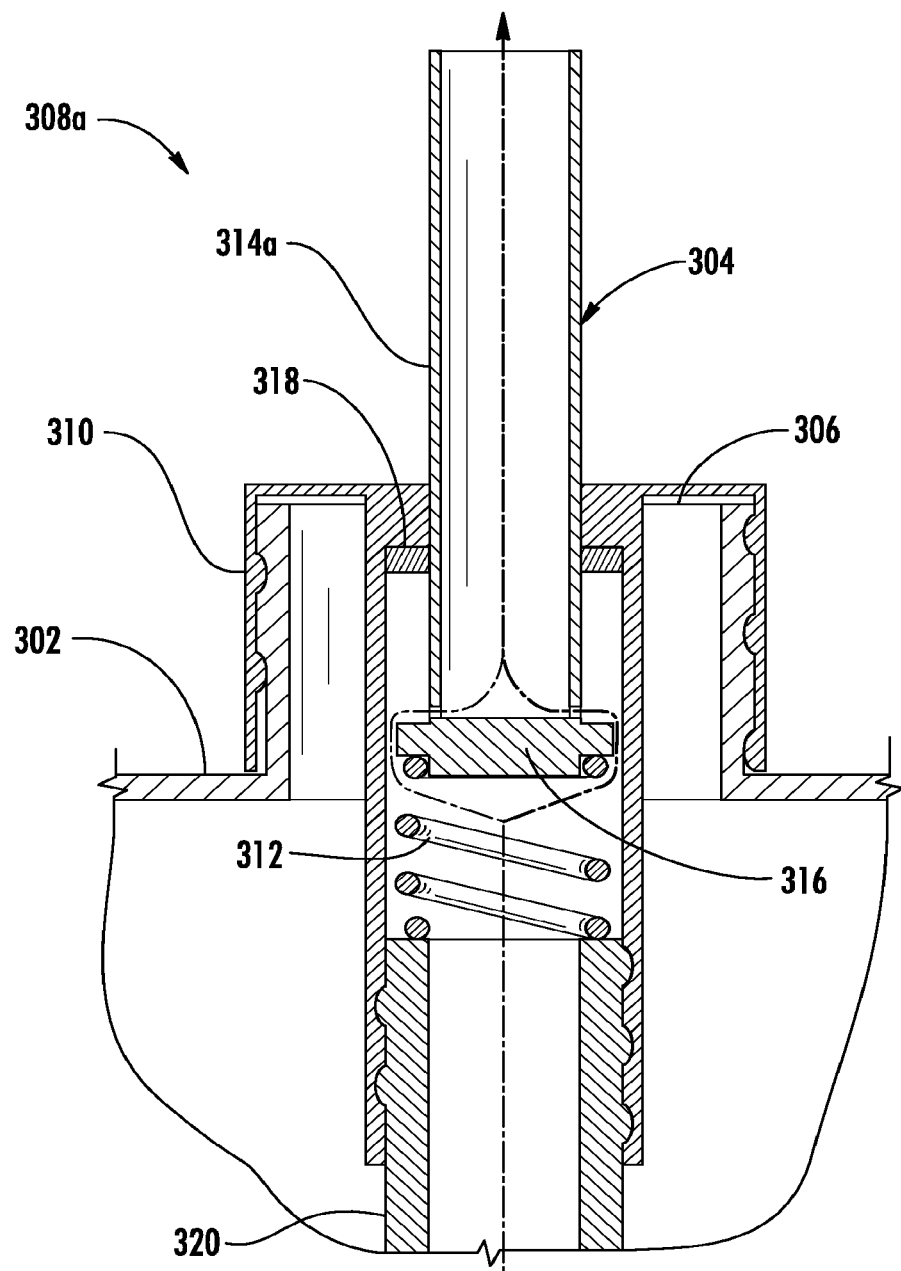
Figure 8:
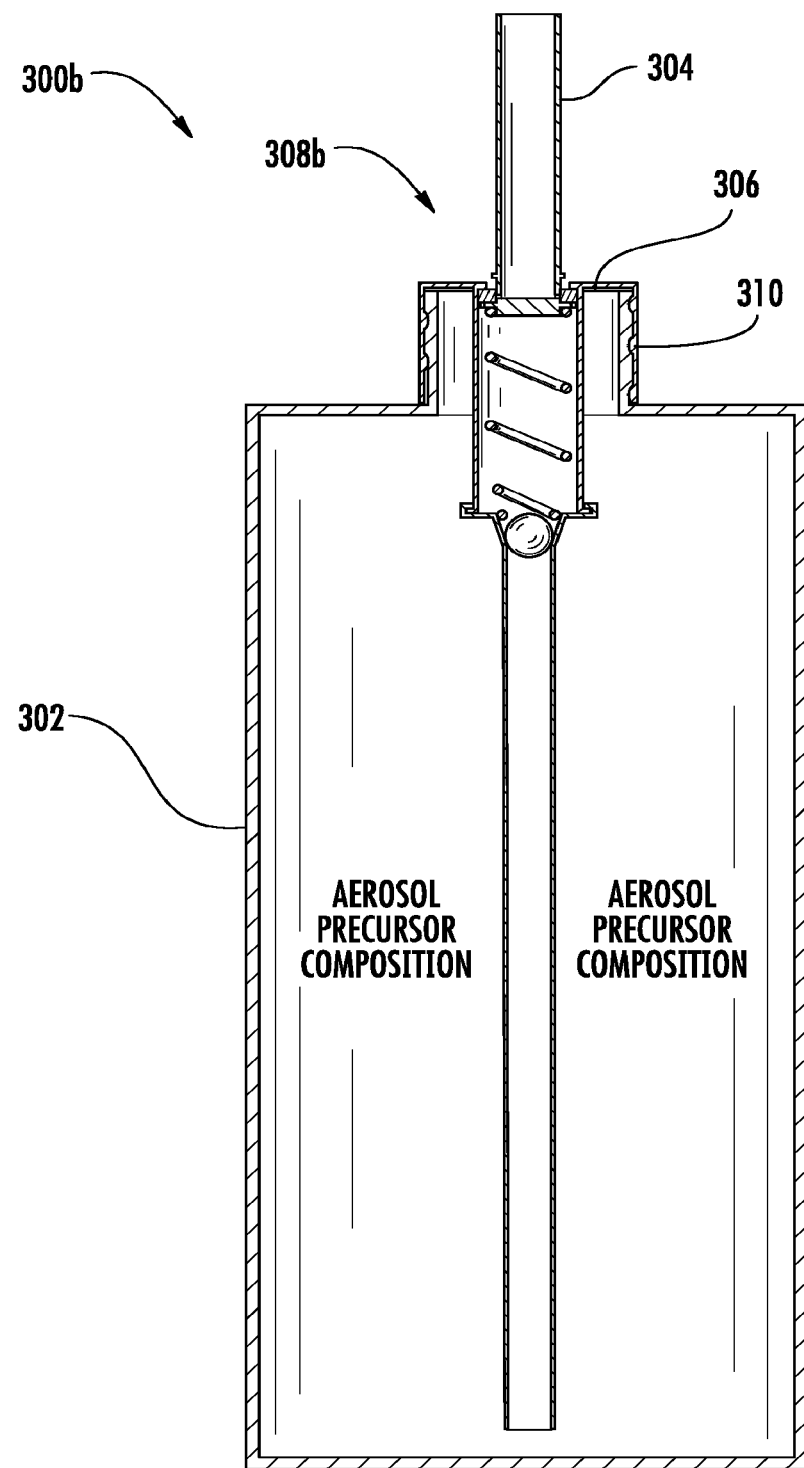
Figure 9:
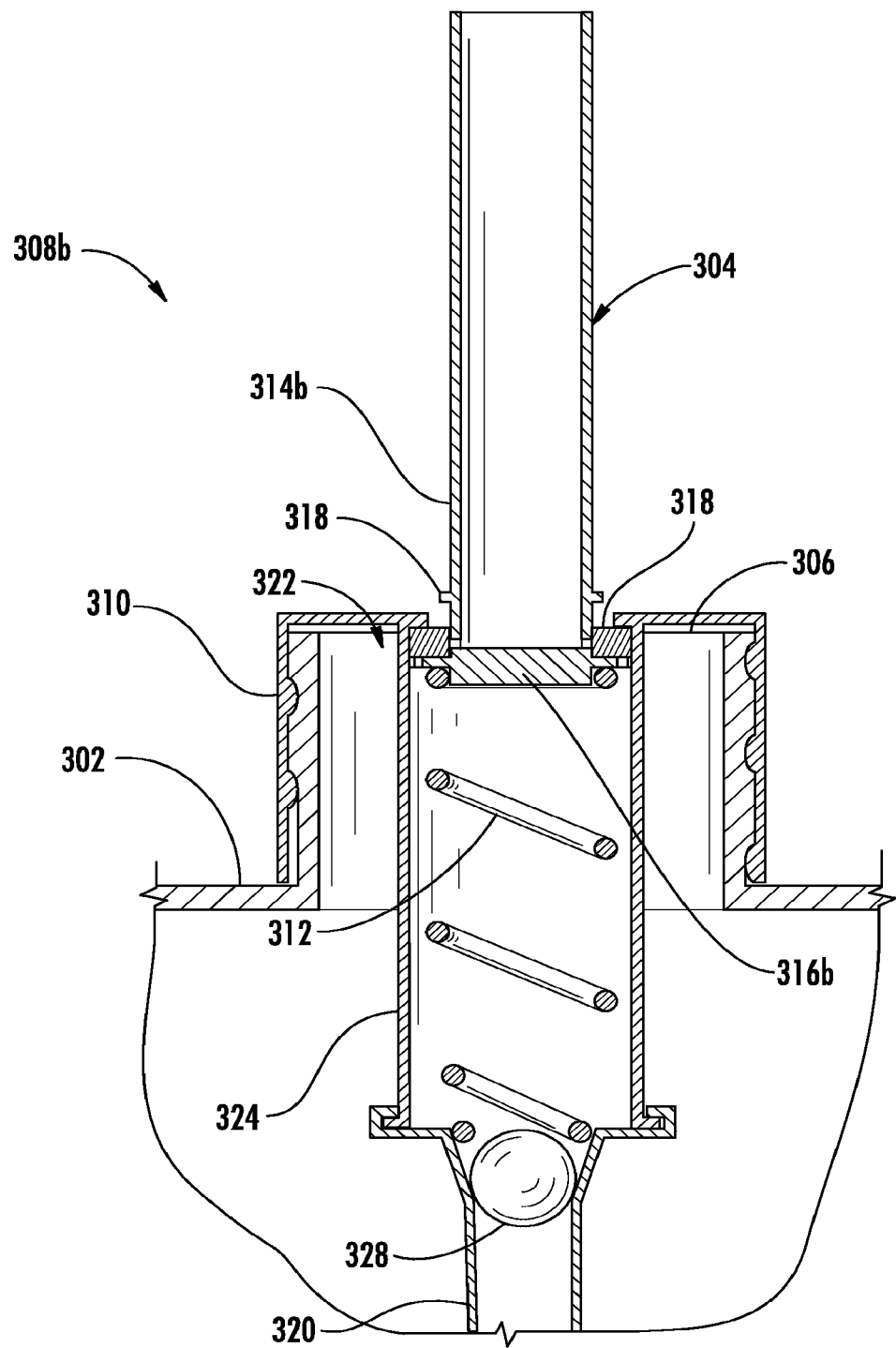
Figure 10:
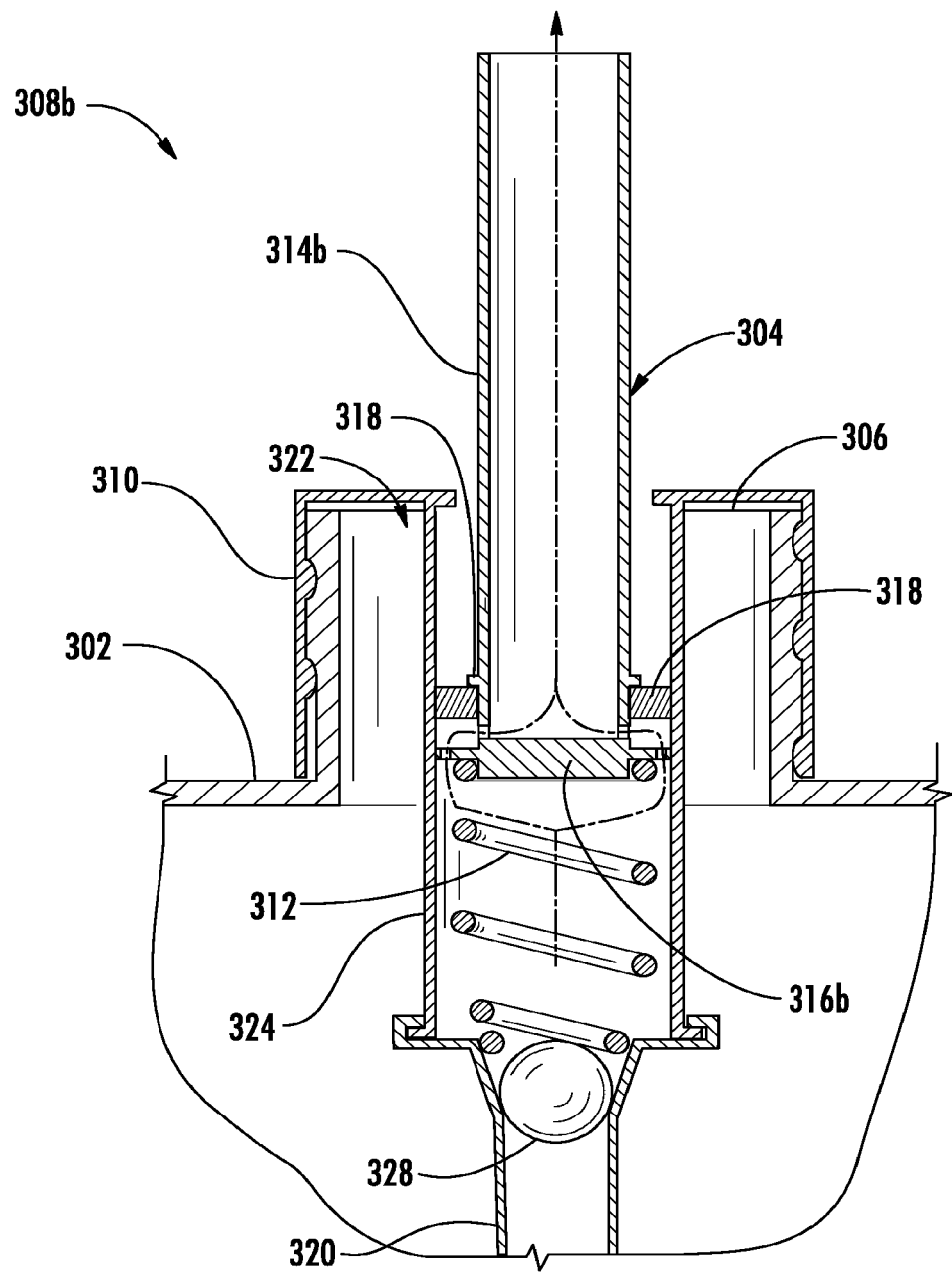
Figure 11:
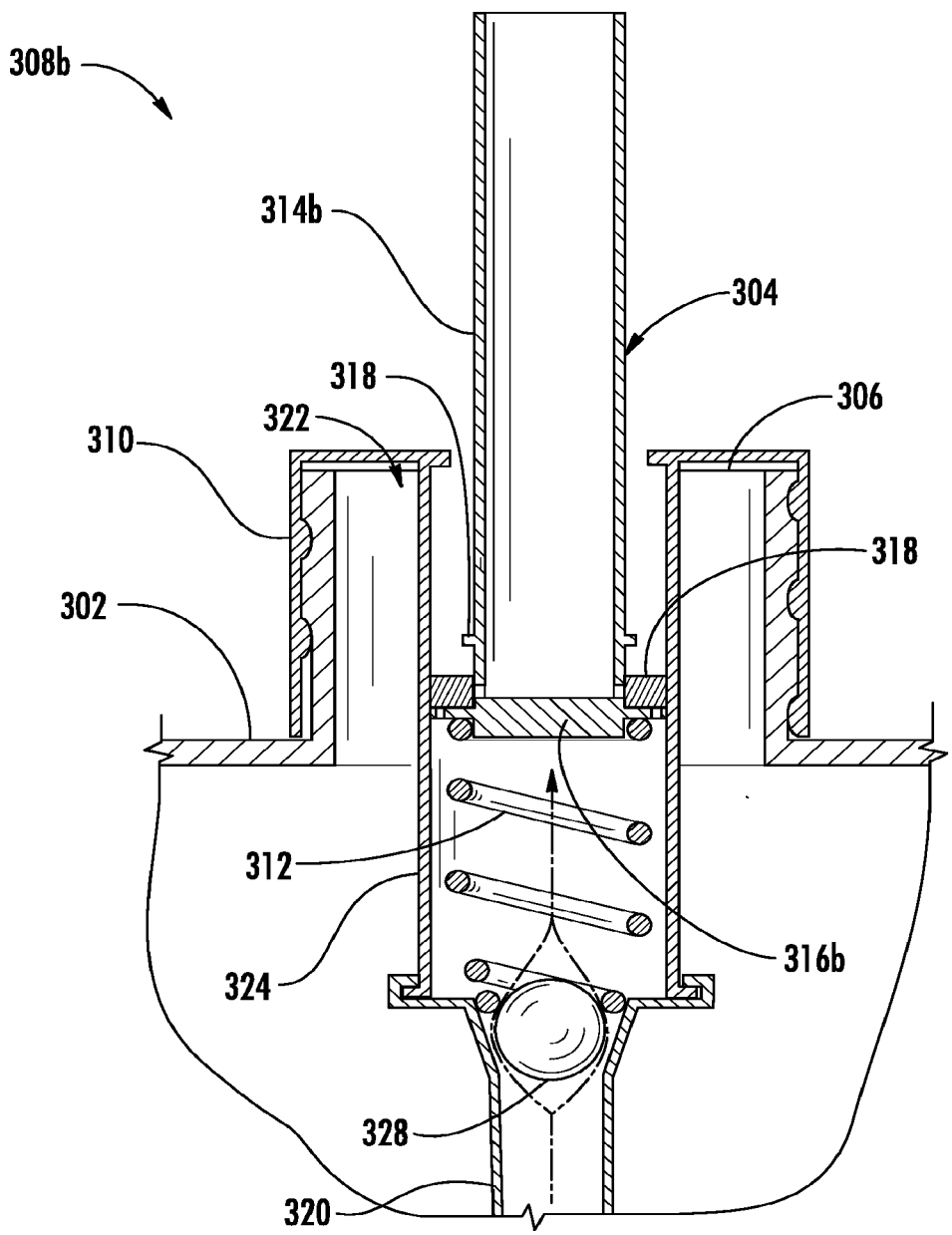
Figure 12:
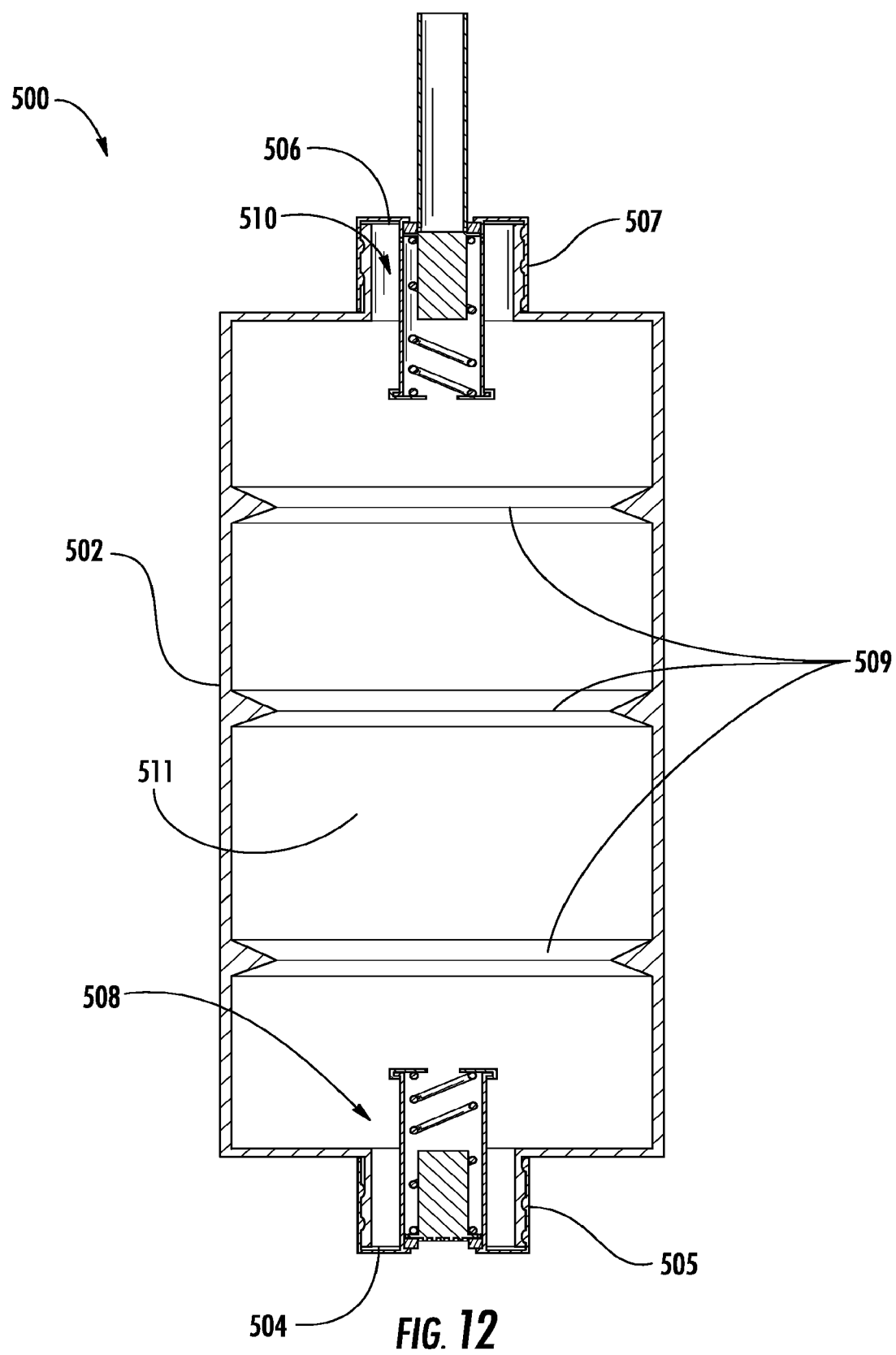
Figure 13:
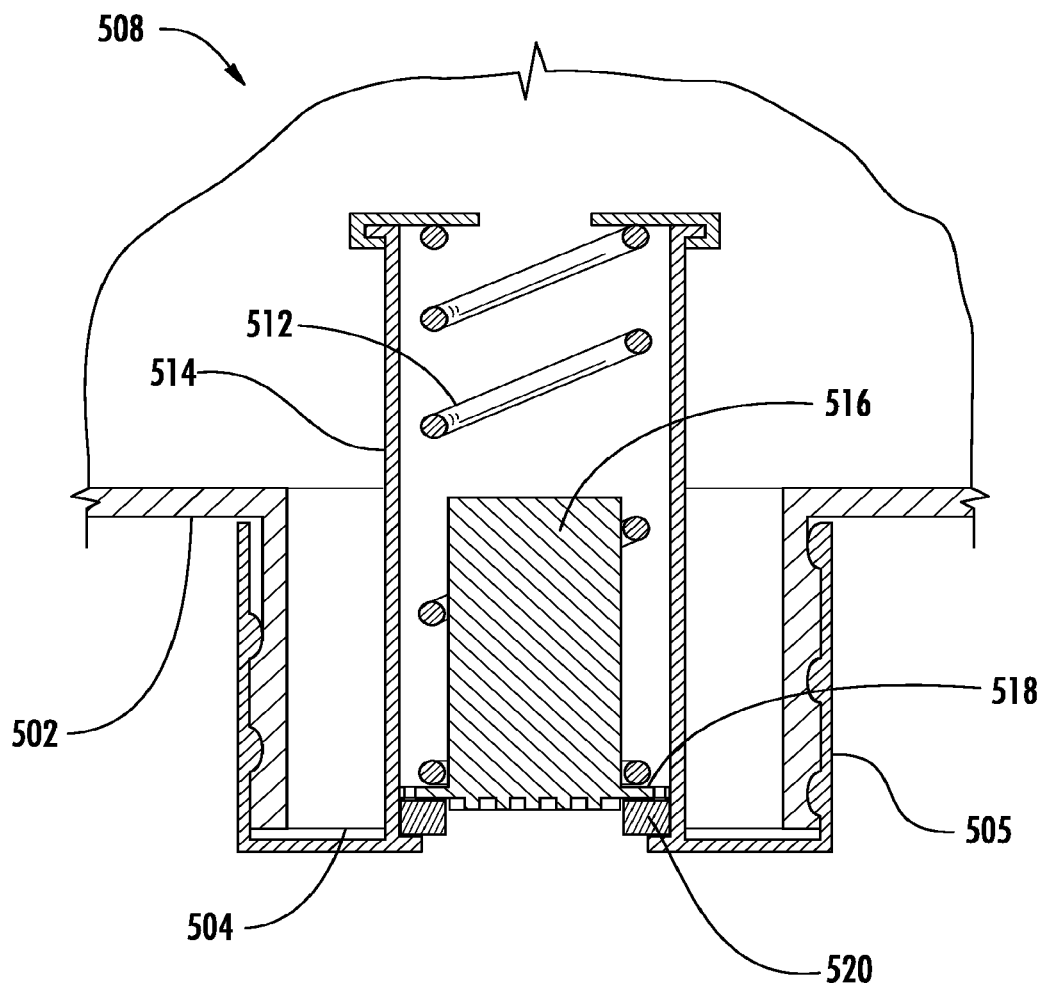
Figure 14:
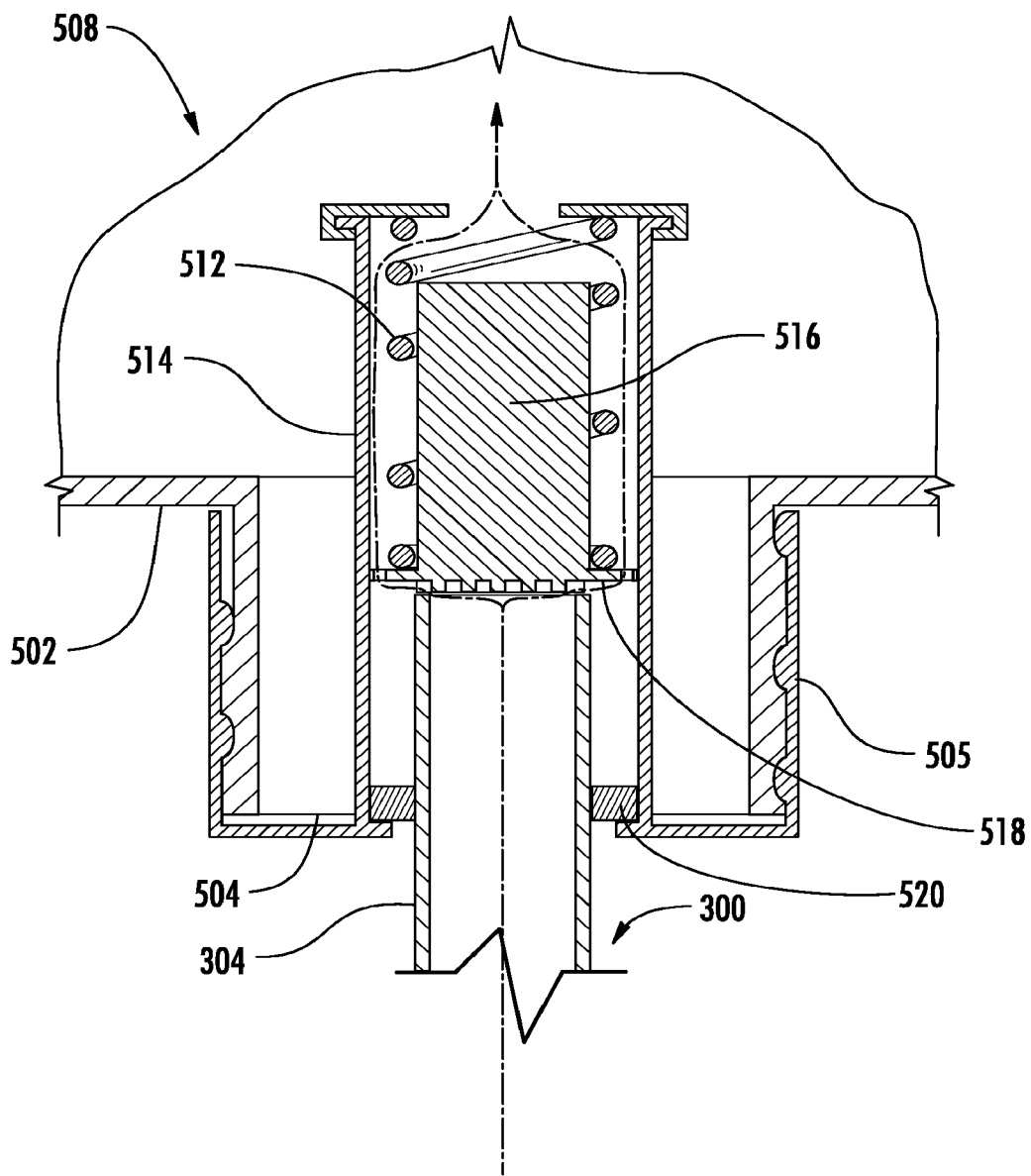
Figure 15:
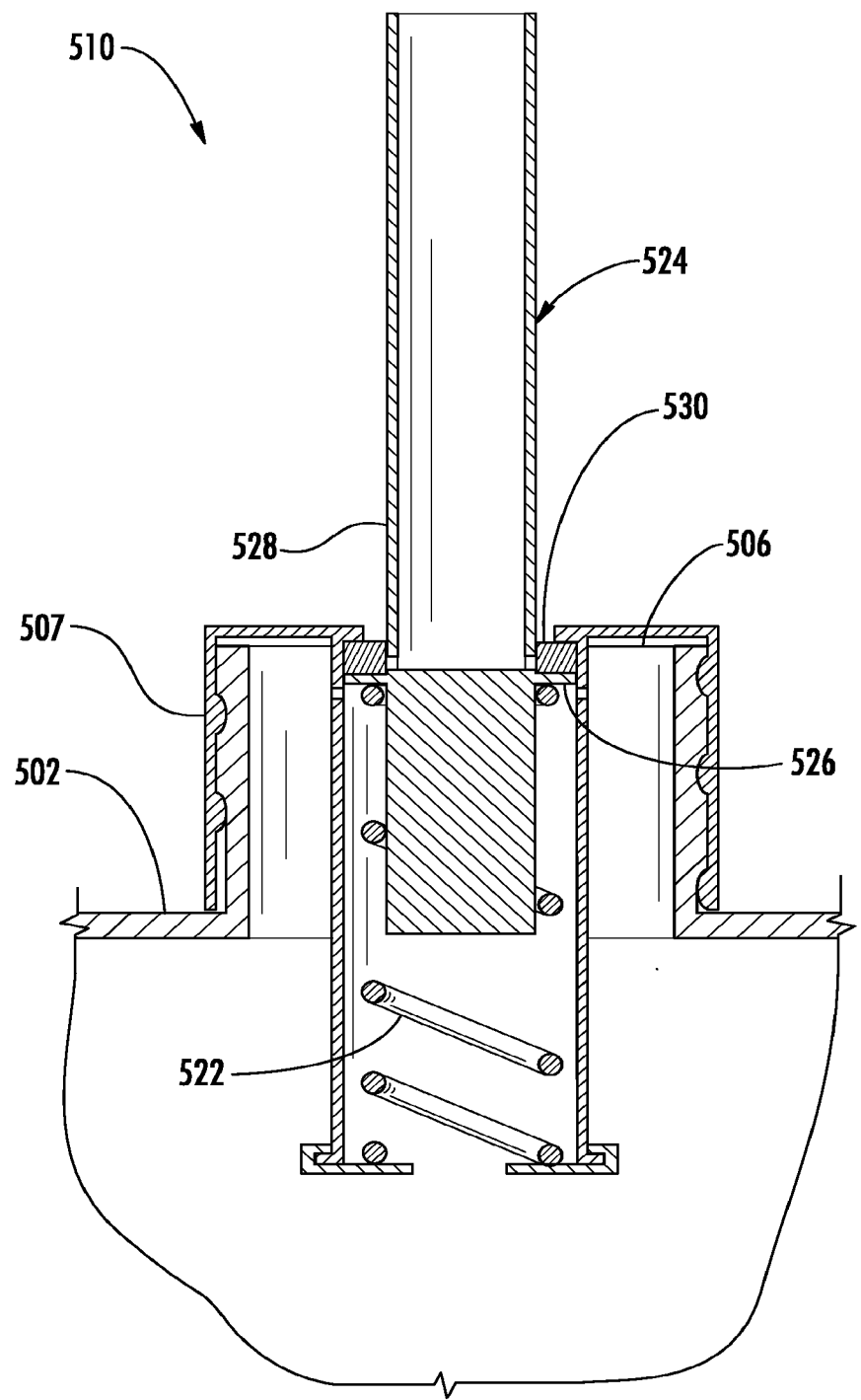
Figure 16:
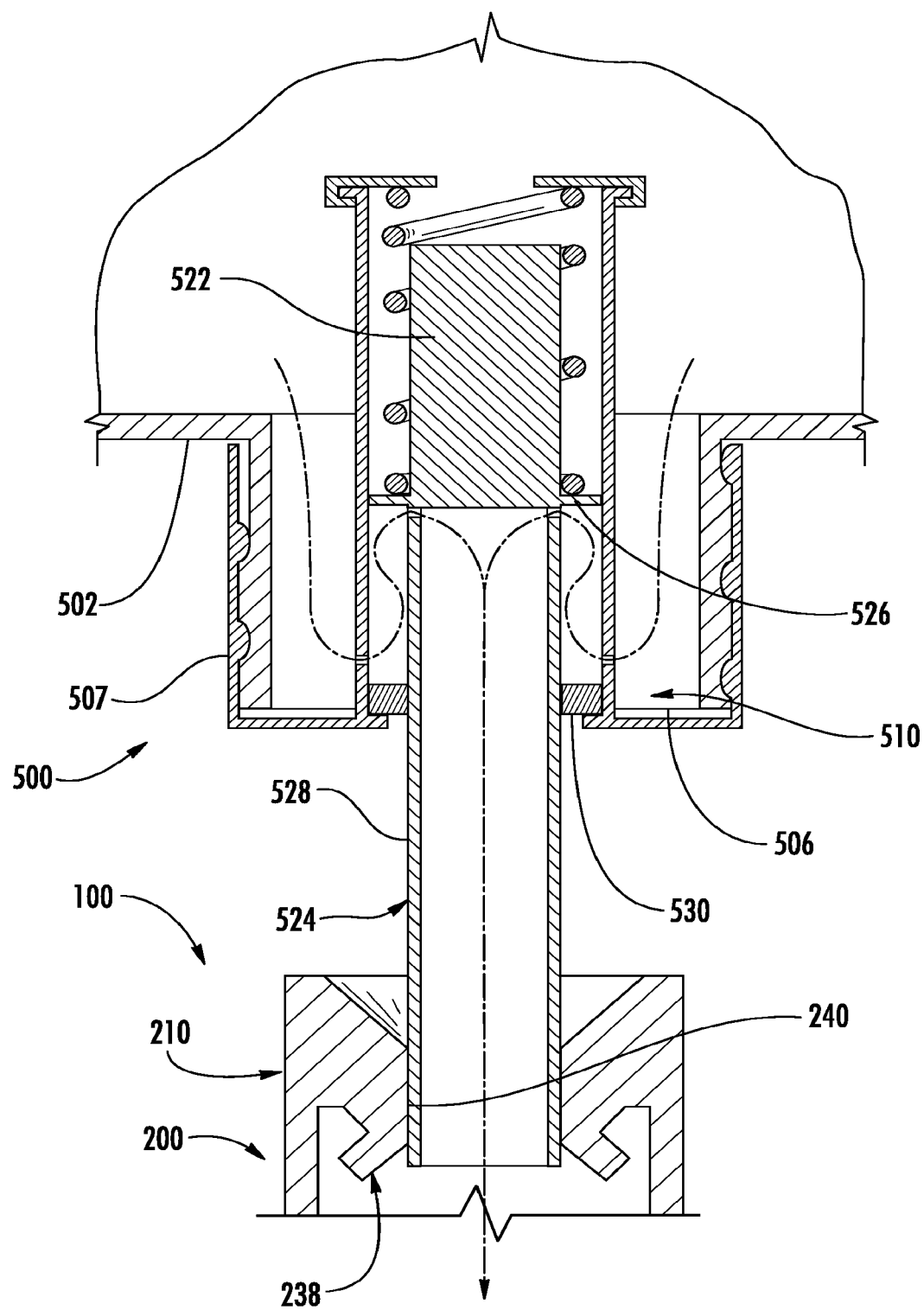
Figure 17:
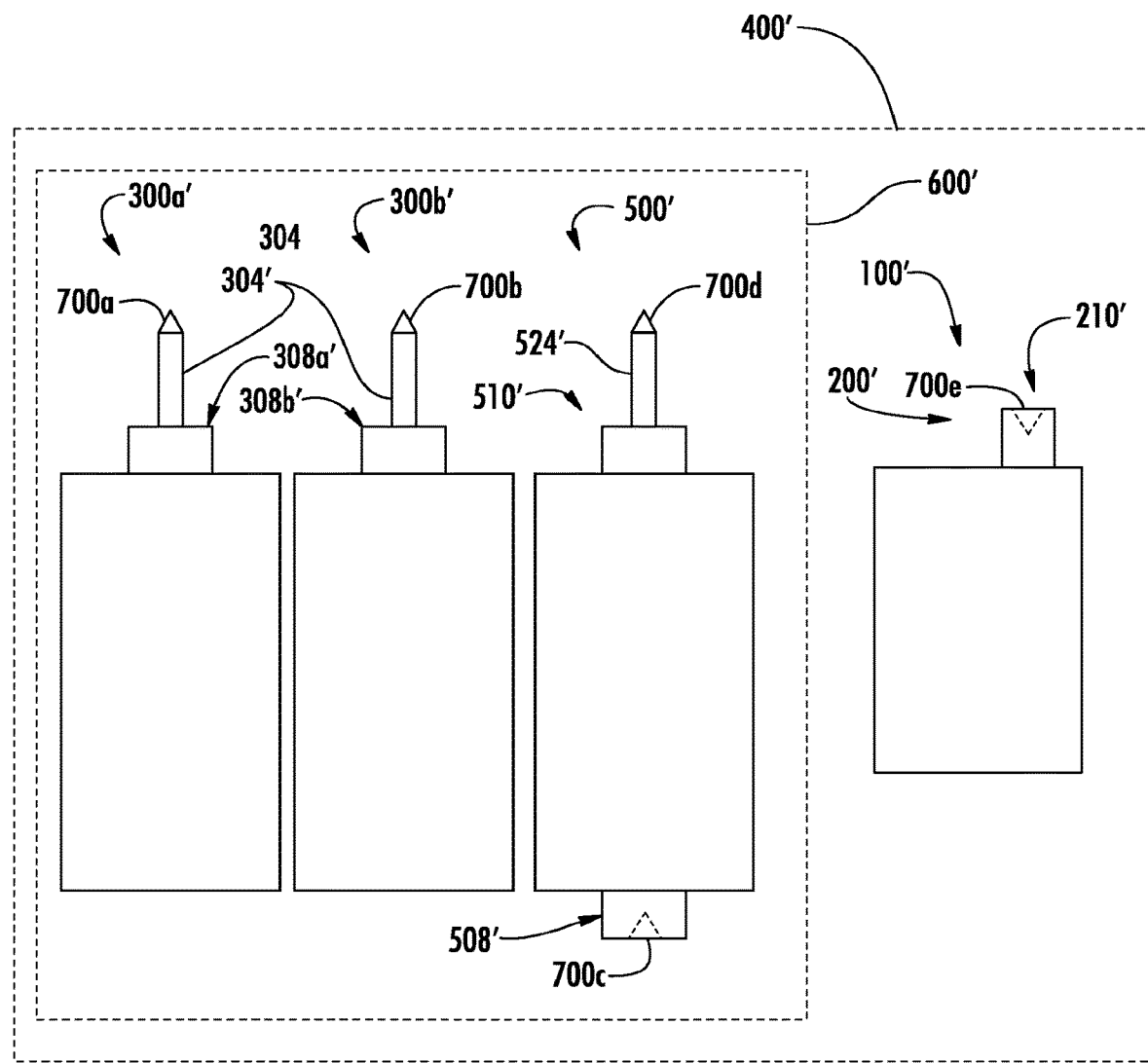

Having thus described the disclosure in the foregoing general terms, reference will now be made to the accompanying drawings, which are not necessarily drawn to scale, and wherein:

FIG. 1 illustrates a side view of an aerosol delivery device including a control body and a cartridge according to an example embodiment of the present disclosure;

FIG. 2 illustrates a partial sectional view through the cartridge of FIG. 1 according to an example embodiment of the present disclosure;

FIG. 3 illustrates a side view of a source container according to an example embodiment of the present disclosure;

FIG. 4 illustrates a side view of an aerosol precursor composition mixing system according to an example embodiment of the present disclosure, the system including first and second source containers, a mixing container, and an aerosol delivery device;

FIG. 5 illustrates a sectional view through the first source container of FIG. 4 according to an example embodiment of the present disclosure;

FIG. 6 illustrates a partial sectional view through the first source container of FIG. 5 wherein a source container outlet valve thereof is in a closed configuration according to an example embodiment of the present disclosure;

FIG. 7 illustrates a partial sectional view through the first source container of FIG. 5 wherein the source container outlet valve is in an open configuration according to an example embodiment of the present disclosure;

FIG. 8 illustrates a sectional view through the second source container of FIG. 4 according to an example embodiment of the present disclosure;

FIG. 9 illustrates a partial sectional view through the second source container of FIG. 8 wherein a source container outlet valve thereof is in a closed configuration according to an example embodiment of the present disclosure;

FIG. 10 illustrates a partial sectional view through the second source container of FIG. 8 wherein the source container outlet valve is in a dispensing configuration according to an example embodiment of the present disclosure;

FIG. 11 illustrates a partial sectional view through the second source container of FIG. 8 wherein the source container outlet valve is in a priming configuration according to an example embodiment of the present disclosure;

FIG. 12 illustrates a sectional view through the mixing container of FIG. 4 according to an example embodiment of the present disclosure;

FIG. 13 illustrates a partial sectional view through the mixing container of FIG. 12 wherein a mixing container inlet valve thereof is in a closed configuration according to an example embodiment of the present disclosure;

FIG. 14 illustrates a partial sectional view through the mixing container of FIG. 12 wherein the mixing container inlet valve is in an open configuration and engaged with an extension of a source container according to an example embodiment of the present disclosure;

FIG. 15 illustrates a partial sectional view through the mixing container of FIG. 12 wherein a mixing container outlet valve thereof is in a closed configuration according to an example embodiment of the present disclosure;

FIG. 16 illustrates a partial sectional view through the mixing container of FIG. 12 wherein the mixing container outlet valve is in an open configuration and engaged with a an aerosol delivery device according to an example embodiment of the present disclosure;

FIG. 17 illustrates a side view of an aerosol precursor composition mixing system according to an example embodiment of the present disclosure, the system including first and second source containers, a mixing container, and an aerosol delivery device, each including a connector; and FIG. 18 schematically illustrates a method for customizing an aerosol precursor composition according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, the present disclosure is directed to an accessory for an aerosol delivery device. The accessory may be employed with various embodiments of aerosol delivery devices. Accordingly, it should be understood that the aerosol delivery devices discussed herein are described by way of example only, and the accessory may be employed with various other embodiments of aerosol delivery devices.

Aerosol delivery devices according to the present disclosure may use electrical energy to heat a material (preferably without combusting the material to any significant degree) to form an inhalable substance; such articles most preferably being sufficiently compact to be considered "hand-held" devices. In highly preferred embodiments, aerosol delivery devices may incorporate tobacco and/or components derived from tobacco. As such, the aerosol delivery device can be characterized as an electronic smoking article such as an electronic cigarette. For purposes of simplicity, the term "aerosol" as used herein is meant to include vapors, gases and aerosols of a form or type suitable for human inhalation, whether or not visible, and whether or not of a form that might be considered to be smoke-like.

By way of example, FIG. 1 illustrates a side view of an aerosol delivery device 100 according to an example embodiment of the present disclosure. As illustrated, the aerosol delivery device 100 may include a control body 101, which may include a housing 102. As further illustrated in FIG. 1, the aerosol delivery device 100 may additionally include a cartridge 200, which may be at least partially received in the control body 101.

The control body 101 may include one or more components. The components may be received in, or otherwise engaged with, the housing 102. For example, the components may include an electrical circuit. An electrical power source may be received in the housing 102. Further, the electrical circuit may include a controller, electrical contacts, and a coupler configured to engage the cartridge 200. In some embodiments the electrical circuit may additionally include an electronic display. Further, the electrical circuit may include a flow sensor configured to direct current to the cartridge 200 to produce an aerosol when a puff on the cartridge is detected. However, in other embodiments the electrical circuit may include a manually-actuated switch that directs current to the cartridge 200.

Examples of electrical power sources are described in U.S. Pat. App. Pub. No. 2010/0028766 to Peckerar et al., the disclosure of which is incorporated herein by reference in its entirety. Further, representative current regulating components and other current controlling components including various microcontrollers, sensors, and switches for aerosol delivery devices are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al.; U.S. Pat. No. 8,205,622 to Pan; and U.S. Pat. No. 8,881,737 to Collet et al.; U.S. Pat. Pub. Nos. 2009/0230117 to Fernando et al.; and 2014/0270727 to Ampolini et al.; and 2015/0257445 to Henry et al.; which are incorporated herein by reference in their entireties. Additional representative types of sensing or detection mechanisms, structures, components, configurations, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

Various elements that may be included in the housing are described in U.S. App. Pub. No. 2015/0245658 to Worm et al., which is incorporated herein by reference in its entirety. Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to a pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 to Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon;

U.S. Pat. No. 8,794,231 to Thorens et al.; U.S. Pat. No. 8,851,083 to Oglesby et al.; U.S. Pat. Nos. 8,915,254; 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety.

A partial sectional view through an example embodiment of the cartridge 200 that may be included in the aerosol delivery device 100 is illustrated in FIG. 2. In some embodiments the cartridge 200 may also be referred to as a tank. In this regard, cartridges including a relatively larger capacity may be referred to as tanks. As illustrated, the cartridge 200 may include an outer body 204 defining a reservoir therein 206. The reservoir 206 may be configured to receive an aerosol precursor composition.

The aerosol precursor composition, also referred to as a vapor precursor composition, may comprise a variety of components including, by way of example, any of a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference in their entireties. Other aerosol precursor compositions which may be employed in the aerosol delivery device of the present disclosure include the aerosol precursors included in the VUSE® product by R. J. Reynolds Vapor Company, the BLU™ product by Lorillard Technologies, the Mistic Menthol product by Mistic Ecigs, and the Vype product by CN Creative Ltd. Also desirable are the so-called "Smoke Juices" for electronic cigarettes that have been available from Johnson Creek Enterprises LLC. Additional exemplary formulations for aerosol precursor compositions that may be used according to the present disclosure are described in U.S. Pat. Pub. No. 2013/0008457 to Zheng et al., and U.S. Pat. No. 9,254,002 to Chong et al., the disclosures of which are incorporated herein by reference in their entireties.

The cartridge 200 may additionally include a mouthend cap 208 that may engage the outer body 204. The cartridge 200 may further include a valve assembly 210 that may allow for receipt of an aerosol precursor composition into the cartridge and exit of aerosol therefrom.

As illustrated in FIG. 2, the cartridge 200 may further comprise an atomizer 212. The atomizer 212 may include a heating element 214 and first and second heating terminals 216a, 216b coupled thereto. Further, the atomizer 212 may include a liquid transport element 218. In some embodiments the liquid transport element 218 may extend around, and be supported by, the first heating terminal 216a.

The liquid transport element 218 may be configured to direct the aerosol precursor composition from the reservoir 206 to the heating element 214. In this regard, the liquid transport element 218 may comprise a wick configured to draw the fluid to the heating element 214 via a mechanism such as capillary action. Thereby, current provided by the control body 101 (see, e.g., FIG. 1) may be directed through a circuit including the first heating terminal 216a, the heating element 214, and the second heating terminal 216b. The internal resistance of the heating element 214 may thereby produce heat that heats the aerosol precursor composition directed thereto by the liquid transport element 218 to produce an aerosol. In some embodiments the heating element 214 may comprise a wire defining a plurality of coils extending around the liquid transport element 218.

The heating element 214 may be positioned in a heating chamber 220 defined by an insert 222. The insert 222 may be engaged with, and at least partially received in, the mouthend cap 208. A sealing member 224 may separate the heating chamber 220 from the reservoir 206 and the aerosol precursor composition received therein.

Aerosol produced in the heating chamber 220 may be directed to the user thereof. In this regard, the insert 222 may include one or more outlet channels 226, and the mouthend cap 208 may define aligned channels 228 that align with the outlet channels 226 of the insert 222. Further, the valve assembly 210 may define one or more outlet apertures 230 that align with the aligned channels 228 extending through the mouthend cap 208. In some embodiments the cartridge 200 may further comprise a mouthpiece configured to direct the aerosol to the user. In this regard, after the aerosol exits the outlet apertures 230, the aerosol may be directed through one or more notches 234 defined at the top of the valve assembly 210 and outwardly through the mouthpiece.

In some embodiments it may be desirable to configure aerosol delivery devices such that the aerosol precursor composition may be refilled. For example, it may be desirable to configure the cartridge 200 to be refillable. In this regard, the valve assembly 210 may include a one-way valve configured to allow flow of aerosol precursor composition into the reservoir and prevent flow of aerosol precursor composition out of the reservoir. As may be understood, a variety of embodiments of one-way valves may be employed. However, in the illustrated embodiment, the one-way valve comprises a diaphragm check valve 238 including a flexible diaphragm. For example, the diaphragm check valve 238 may comprise silicone, rubber, or another resilient material. The diaphragm check valve 238 may define a passageway 240 that is biased to a closed configuration and configured to flex open and thereby allow flow through the passageway in response to application of an external positive pressure or engagement of a tube therewith. Accordingly, aerosol precursor composition may be directed through the valve assembly 210 and into the reservoir 206 while the diaphragm check valve 238 is open. In this regard, the mouthend cap 208 and/or the insert 222 may define a fill channel extending between an inlet chamber 244 and the reservoir 206. Thereby, aerosol precursor composition directed through the one-way valve 238 may be directed through the inlet chamber 244 to the reservoir 206.

However, after the positive pressure and/or tube is removed, the diaphragm check valve 238 may return to the closed configuration. Further, the diaphragm check valve 238 may be configured such that drawing on the mouthpiece further seals the passageway 240. Thereby, draw on the mouthpiece may direct aerosol to the user without directing fluid aerosol precursor composition to the user.

Various other embodiments of one-way valves that may be included in refillable cartridges are described in U.S. patent application Ser. No. 15/088,323 to Davis et al., filed Jan. 27, 2016, which is incorporated herein by reference in its entirety. Further, U.S. patent application Ser. No. 14/802,667 to O'Brien et al., filed Jul. 17, 2015, discloses an aerosol delivery device including a refillable reservoir and a container for refilling the reservoir and is incorporated herein by reference in its entirety.

Representative types of substrates, reservoirs, or other components for supporting the aerosol precursor are described in U.S. Pat. No. 8,528,569 to Newton and U.S. Pat. No. 8,715,070 to Davis et al.; and U.S. Pat. App. Pub. Nos. 2014/0261487 to Chapman et al. and 2015/0216232 to Bless et al., which are incorporated herein by reference in their entireties. Various wicking materials, and the configuration and operation of those wicking materials within certain types of aerosol delivery devices, are set forth in U.S. Pat. No. 8,910,640 to Sears et al., which is incorporated herein by reference in its entirety. A variety of the materials disclosed by the foregoing documents may be incorporated into the present devices in various embodiments, and all of the foregoing disclosures are incorporated herein by reference in their entireties.

In some embodiments the heating element may be formed by winding the wire about the liquid transport element as described in U.S. Pat. No. 9,210,738 to Ward et al, which is incorporated herein by reference in its entirety. Further, in some embodiments the wire may define a variable coil spacing, as described in U.S. Pat. No. 9,277,770 to DePiano et al., which is incorporated herein by reference in its entirety. An example embodiment of a mesh heating element is disclosed in U.S. Pat. Appl. Pub. No. 2015/0034103 to Hon. In some embodiments, a stamped heating element may be employed in the atomizer, as described in U.S. Pat. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above. Additionally, embodiments of microheaters and atomizers incorporating microheaters suitable for use in the presently disclosed devices are described in U.S. Pat. No. 8,881,737 to Collett et al., which is incorporated herein by reference in its entirety. Further, various examples of electronic control components and functions performed thereby are described in U.S. Pat. App. Pub. No. 2014/0096781 to Sears et al., which is incorporated herein by reference in its entirety. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety. An example embodiment of a carbon-based cartridge is provided in U.S. Pat. App. Pub. No. 2013/0255702 to Griffith et al., which is incorporated herein by reference in its entirety.

Additional features and components of the aerosol delivery device are provided in U.S. patent application Ser. No. 14/981,051 to Phillips et al., filed Dec. 28, 2015, which is incorporated herein by reference in its entirety. Further, it should be understood that the description included above is provided for example purposes only. In this regard, the cartridges, systems, apparatuses, and methods described hereinafter may be employed with various embodiments of aerosol delivery devices.

Accordingly the cartridge 200 described above may be refilled with aerosol precursor composition. In this regard, FIG. 3 illustrates a source container 300. The source container 300 may include a source container body 302 and an extension 304. The extension 304 may be configured to engage the valve assembly 210 of the cartridge 200 to fill the reservoir 206 with an aerosol precursor composition (see, FIG. 2).

However, it may be desirable for a user to mix his or her own aerosol precursor compositions for usage in the cartridge. In this regard, it may be desirable to mix two or more aerosol compositions to obtain a desired nicotine content or flavor, and strength thereof. Although so-called "vape shops" may sell custom aerosol precursor compositions, purchasing such aerosol precursor compositions may be expensive and/or inconvenient for a user. Further, when a user purchases custom aerosol precursor compositions from a store, it may be impossible for the user to verify the source of the aerosol precursor composition components. Thereby, a user may not be assured that the aerosol precursor composition comes from known sources.

Accordingly, a user may prefer to mix his or her own aerosol precursor composition. Thereby, the user may purchase known aerosol precursor compositions from known manufacturers such that issues with respect to unknown ingredients and/or quality control issues may be avoided. Further, the user may tailor the mixed aerosol precursor composition to his or her specific tastes. However mixing custom aerosol precursor compositions may be messy and/or wasteful.

Thus, as illustrated in FIG. 4, embodiments of the present disclosure provide an aerosol delivery device filling system 400. The aerosol delivery device filling system 400 may include a plurality of source containers 300. For example, in the illustrated embodiment the aerosol delivery device filling system 400 includes a first source container 300a and a second source container 300b. The first source container 300a may include a first aerosol precursor composition and the second container 300b may include a second aerosol precursor composition, which may differ from the first aerosol precursor composition in one or more respects. However, as may be understood, additional source containers 300 may be employed in other embodiments.

The aerosol delivery device filling system 400 may additionally include the aerosol delivery device 100. As noted above, in some embodiments the source containers 300 may be configured to directly engage the aerosol delivery device 100 to fill the aerosol delivery device with aerosol precursor composition. However, in another embodiment the aerosol delivery device filling system 400 may additionally include a mixing container 500. The mixing container 500 may be configured to engage the first source container 300a to receive at least a portion of the first aerosol precursor composition and engage the second source container 300b to receive at least a portion of the second aerosol precursor composition to form a mixed aerosol precursor composition. The mixing container 500 and the plurality of source containers 300 may collectively define an aerosol precursor composition mixing system 600.

The aerosol delivery device 100 may be configured to engage the mixing container 500 to receive at least a portion of the mixed aerosol precursor composition. Accordingly, a user may employ the source containers 300 and the mixing container 500 to mix the aerosol precursor compositions included in the source containers to produce a mixed aerosol precursor composition, rather than purchasing the mixed aerosol composition from a vape shop or other source.

As may be understood, various embodiments of the source containers 300 may be employed. However, by way of example, FIG. 5 illustrates a sectional view through the source container 300a. As illustrated therein, the source container body 302 may define a source container outlet 306. A source container outlet valve 308a may be coupled to the source container outlet 306. For example, the source container outlet valve 308a may be engaged with a cap 310 covering the source container outlet 306.

The source container outlet valve 308a may comprise a one-way valve configured to selectively allow flow of aerosol precursor composition out of the source container body 302. In one embodiment the source container outlet valve 308a may be configured to open when the extension 304 is depressed. As further illustrated in FIG. 5, in one embodiment the source container body 302 may further include a pressurized propellant. The pressurized propellant may be configured to expel the aerosol precursor composition from the source container body 302 when the source container outlet valve 308a is opened.

In this regard, FIGS. 6 and 7 illustrate operation of the source container outlet valve 308a. In particular, FIG. 6 illustrates the source container outlet valve 308a in a closed configuration and FIG. 7 illustrates the source container outlet valve in an open configuration. As illustrated in FIGS. 6 and 7, the source container outlet valve 308a may include a spring 312 configured to bias the one-way valve to a closed configuration. In this regard, the extension 304 may include an outlet tube 314a that extends out of the source container body 302 and a flange 316a. The spring 312 may bias the flange 316a of the extension 304 into engagement with a sealing member 318 (e.g., a resilient O-ring). Thereby, flow of the aerosol precursor composition out through the source container outlet valve 308a may be resisted.

However, when the extension 304 is depressed, the flange 316a may release from the sealing member 318 to define the open configuration illustrated in FIG. 7. Thereby, the pressurized propellant may force the aerosol precursor composition up through a dip tube 320 and into the source container outlet valve 308a and out the outlet tube 314a of the extension 304. Once the extension 304 is released such that it is no longer depressed, the spring 312 may return the extension to the closed configuration illustrated in FIG. 6 in which the flange 316a seals against the sealing member 318.

FIG. 8 illustrates a sectional view through the second source container 300b. As illustrated the second source container 300b may include the source container body 302, the source container outlet 306, a source container outlet valve 308b including an extension 304, and the cap 310 covering the source container outlet. Accordingly, the second source container 300b may be substantially similar to that of the first source container 300a (see, e.g., FIG. 7).

Further, the source container outlet valve 308b may comprise a one-way valve. However, the particular configuration of the source container outlet valve 308b may differ. In this regard, whereas the source container outlet valve 308a of the first source container 300a (see, e.g., FIG. 5) is configured to employ a pressurized propellant to dispense the aerosol precursor composition, the source container outlet valve 308b of the second source container 300b may be configured to pump the aerosol precursor composition into the mixing container 500 (see, e.g., FIG. 4).

In this regard, FIGS. 9-11 illustrate operation of the source container outlet valve 308b. In particular, FIG. 9 illustrates the source container outlet valve 308b in a closed configuration, FIG. 10 illustrates the source container outlet valve during depression of the extension 304 and dispensing, and FIG. 11 illustrates return of the extension 304 to the closed configuration and priming. The source container outlet valve 308b may comprise a pump mechanism 322 configured to pump the aerosol precursor composition into the mixing container 500 (see, e.g., FIG. 4). The pump mechanism 322 may include a flange 316b of the extension 304 and a valve body 324 in which the flange is received. A spring 312 may engage the flange 316b of the extension 304 to bias the one-way valve to the closed configuration illustrated in FIG. 9. In this regard, the extension 304 may include an outlet tube 314b that extends out of the source container body 302 and the flange 316b. The spring 312 may bias the flange 316b of the extension 304 into engagement with a sealing member 318 (e.g., a resilient ring-shaped gasket). Thereby, flow of the aerosol precursor composition out through the source container outlet valve 308b may be resisted.

However, as illustrated in FIG. 10, when the extension 304 is depressed, the sealing member 318 may slide along the extension until it contacts a stop 326. Thereby, the flange 316b may release from the sealing member 318 to define an open dispensing configuration. In this regard, the valve body 324 maybe sealed at the lower end thereof by a ball 328. Accordingly, as the extension 304 is depressed downwardly, a volume of a cavity in which the spring 312 is positioned within the valve body 324 may decrease, thereby producing a positive pressure in the valve body that forces the aerosol precursor therein out of the cavity through or around the flange 316b and out of the outlet tube 314b.

As illustrated in FIG. 11, after the depression of the extension 304 is complete, the spring 312 may return the extension 304 to the closed configuration. In this regard, as the extension 304 is directed back toward the initial starting position (see, FIG. 9), the sealing member 328 may slide along the extension back into engagement with the flange 316, thereby preventing flow therethrough. Thereby, a low pressure is produced in the cavity in the valve body 324 in which the spring 312 is positioned as the spring elongates. Thereby, the ball 326 may lift off of the valve body 324, which allows flow of the aerosol precursor composition from the source container body 302 through a dip tube 322 into the cavity in the valve body in which the spring 312 is positioned. Thus, the valve body 324 may fill with the aerosol precursor composition such that the source container outlet valve 308b is primed for the next depression thereof. Ultimately, the spring 312 returns the source container outlet valve 308 to the initial closed configuration illustrated in FIG. 9.

Accordingly, the source containers 300a, 300b may dispense aerosol precursor compositions, and the mixing container 500 (see, FIG. 4) may be configured to receive the aerosol precursor compositions. In this regard, FIG. 12 illustrates a sectional view through an example embodiment of the mixing container 500. As illustrated, the mixing container 500 may include a mixing container body 502. The mixing container body 502 may define a mixing container inlet 504 and a mixing container outlet 506. A mixing container inlet valve 508 may be coupled to the mixing container inlet 504 via an inlet cap 505. A mixing container outlet valve 510 may be coupled to the mixing container outlet 506 via an outlet cap 507.

The mixing container 500 may be configured to receive aerosol precursor composition from one or more source containers 300 (see, e.g., FIG. 4). In particular, the source container outlet valve 308a, 308b of each source container 300a, 300b (see, e.g., FIGS. 5 and 8) and the mixing container inlet valve 508 may be configured to engage one another and open during engagement to allow transfer of the aerosol precursor composition from the source container body 302 to the mixing container body 502.

In this regard, FIG. 13 illustrates an enlarged view of the mixing container inlet valve 508. The mixing container inlet valve 508 may comprise a one-way valve configured to selectively allow flow into the mixing container body 502 and resist flow outwardly therethrough. In this regard, the mixing container inlet valve 508 may include a spring 512 configured to bias the one-way valve to a closed configuration, which is illustrated in FIG. 13.

Additionally, the mixing container inlet valve 508 may include a receptacle 514. A stopper 516 may be received in the receptacle 514. The stopper 516 may include a flange 518 that is configured to engage a sealing member 520 (e.g. an O-ring). Thereby, flow of aerosol precursor composition out through the mixing container inlet valve 508 may be resisted.

Further, as illustrated in FIG. 13, the mixing container inlet valve 508 may be at least partially recessed within the mixing container body 502. In contrast, the source container outlet valves 308a, 308b (see, e.g., FIGS. 6 and 9) may at least partially extend out of the respective source container body 302. In this regard, as noted above, the source container outlet valves 308a, 308b may include the extension 304.

During filling of the mixing container 500 with aerosol precursor composition from the source containers 300, the source container outlet valve 308a, 308b may engage the mixing container inlet valve 508. In this regard, as illustrated in FIG. 14, the extension 304 of the source container 300 may engage the stopper 516. Thereby, the spring 512 may be compressed and the flange 518 of the stopper 516 may disengage from the sealing member 520 such that the mixing container inlet valve 508 opens as the extension 304 extends into the receptacle 514. As the mixing container inlet valve 508 opens, the source container outlet valve 308a, 308b (see, e.g., FIGS. 6 and 9) may also open. As described above, depressing the extension 304 may open the source container outlet valves 308a, 308b. In this regard, the extension 304 may be depressed during engagement with the mixing container inlet valve 508 such that the mixing container inlet valve 508 and the source container outlet valve each open during engagement of the extension with the receptacle 514. Thereby, the aerosol precursor composition may be directed through the mixing container inlet valve 508 and into the mixing container body 502, as illustrated in FIG. 14.

Thereby, the mixing container 500 may receive aerosol precursor composition from one or more source containers 300. As described above, the aerosol precursor compositions provided by the source containers 300 may differ from one another. Thereby, a user may form a mixed aerosol precursor composition having a desired composition in the mixing container 500 (see, e.g., FIG. 12). In some embodiments a user may shake the mixing container after the aerosol precursor compositions are received therein such that the mixed aerosol precursor composition becomes substantially uniform in composition. In this regard, in some embodiments the mixing container 500 may include one or more surface features 509 at an internal surface 511 thereof. For example, the surface features 509 may comprise grooves, textures, protrusions or any other features extending into and/or away from the internal cavity defined by the mixing container 500 configured to produce turbulence when the mixing container 500 is shaken. In this regard, not all aerosol precursor compositions may readily mix. However, the surface features 509 may facilitate mixing of the fluids by promoting turbulence and mixing action therein.

After the aerosol precursor compositions are received in the mixing container 500, the mixed aerosol precursor composition may be dispensed to the aerosol delivery device 100 (see, e.g., FIG. 4). In this regard, the mixing container outlet valve 510 (see, e.g., FIG. 12) may be configured to open during engagement with the aerosol delivery device 100.

FIGS. 15 and 16 illustrated enlarged views of the mixing container outlet valve 510. In particular FIG. 15 illustrates the mixing container outlet valve 510 in a closed configuration. The mixing container outlet valve 510 may comprise a one-way valve configured to selectively allow flow out of the mixing container body 502 and resist flow inwardly therethrough. In this regard, the mixing container outlet valve 510 may include a spring 522 configured to bias the one-way valve to the closed configuration illustrated in FIG. 15. In particular, the mixing container outlet valve 510 may include an extension 524. The extension 524 may include a flange 526 and an outlet tube 528. The spring 522 may bias the extension 524 such that the flange 526 engages a sealing member 530. Thereby, the mixing container outlet valve 510 may resist flow of aerosol precursor composition therethrough in the closed configuration illustrated in FIG. 15.

FIG. 16 illustrates dispensing of aerosol precursor composition from the mixing container 500 to the cartridge 200 of the aerosol delivery device 100 (see, e.g., FIG. 1). As illustrated, the extension 524 of the mixing container outlet valve 510 may engage the valve assembly 210 of the cartridge 200. In particular, the outlet tube 528 may be received in the passageway 240, thereby opening the diaphragm check valve 238 of the valve assembly 210.

Further, engagement of the extension 524 with the valve assembly 210 may depress the extension. Thereby, the flange 526 of the extension 524 may release from the sealing member 530. Accordingly aerosol precursor composition may travel from the mixing container body 502 through the container outlet valve 510, out the outlet tube 528 and into and through the valve assembly 210 of the cartridge 200 as described above. Accordingly, the cartridge 200 may be filled with the mixed aerosol precursor composition provided by the mixing container 500.

Usage of the mixing container 500 thus provides a convenient way to produce customized aerosol precursor compositions. Further, the configuration of the source containers 300a, 300b, mixing container 500, and aerosol delivery device 100 (see, e.g., FIG. 4) with a one-way valve (e.g., a check valve) at each inlet/outlet may reduce the possibility for spills of the aerosol precursor composition. Note that although mechanisms for dispensing the aerosol precursor composition into the mixing container 500 are generally described as employing pressure to transfer the aerosol precursor composition from the source containers 300a, 300b to the mixing container, in other mechanisms non-pressurized mechanisms may be employed. For example, the aerosol precursor composition may be dispensed via gravity. In other embodiments the source container bodies may be configured to collapse when squeezed by a user to dispense the aerosol precursor composition into the mixing container.

As may be understood, any other embodiment of dispensing mechanism and corresponding method may be employed in other embodiments.

Further, in some embodiments the aerosol delivery device filling system may include features configured to prevent usage of generic source containers to fill the mixing container. Thereby, the aerosol delivery device filling system may prevent filling of the aerosol delivery device with a generic aerosol precursor composition that may not meet desired specifications.

In this regard, FIG. 17 illustrates an additional embodiment of the aerosol delivery device filling system 400'. The aerosol delivery device filling system 400' may include an aerosol precursor composition mixing system 600' and an aerosol delivery device 100'. The aerosol precursor composition mixing system 600' may include a plurality of source containers 300a', 300b' and a mixing container 500'. Accordingly, the aerosol delivery device filling system 400' may be substantially similar to the aerosol delivery device filling system 400 (see, FIG. 4) described above.

However, as schematically illustrated in FIG. 17, the aerosol delivery device filling system 400' may additionally include connectors 700a-e. The connectors 700a-e may be configured to define a specialized size and/or shape such that generic connectors may not be employed to engage and transfer aerosol precursor composition therethrough. For example, the source containers 300a', 300b' may each include a connector 700a, 700b at the extension 304' of the source container outlet valve 308a', 308b'. The connectors 700a, 700b of the source containers 300a', 300b' may be configured to engage a connector 700c at the mixing container inlet valve 508'. Further, the extension 524' of the mixing container outlet valve 510' may include a connector 700d configured to engage a connector 700e at the valve assembly 210' of the cartridge 200' of the aerosol delivery device 100'.

In some embodiments the connectors 700a, 700b of the source containers 300a', 300b' may be configured to engage the connector 700e of the aerosol delivery device 100'. This configuration may be desirable in embodiments in which it is preferable to allow a user to directly refill the aerosol delivery device 100' with a source bottle 300a', 300b'. For example, this configuration may be desirable to allow a user to directly fill the aerosol delivery device with an off-the-shelf aerosol precursor composition. However, in other embodiments the connectors 700a, 700b of the source containers 300a', 300b' may not be configured to connect with the connector 700e of the aerosol delivery device 100'. This configuration may be desirable in embodiments in which it is desirable to require a consumer to purchase the mixing container 500' in order to refill the aerosol delivery device 100'. Accordingly, usage of specialized (e.g., proprietary and/or unique) connectors may allow for greater control over refilling of the aerosol delivery device 100'.

Various other embodiments of connectors may be employed such as threaded connectors, press-fit connectors, interference fit connectors, and magnetic connectors. Further, U.S. patent application Ser. No. 15/042,868 to Davis et al., filed Feb. 12, 2016, discloses connectors for refilling reservoirs of aerosol delivery devices from a container and is incorporated herein by reference in its entirety.

As should be understood, the valves and valve assemblies described above are provided for example purposes only. Various other embodiments of valves and valve assemblies may be employed in accordance with embodiments of the present disclosure.

In an additional embodiment a method for assembling an aerosol delivery device accessory is provided. As illustrated in FIG. 18, the method may include receiving a first aerosol precursor composition from a first source container at operation 802. Further, the method may include receiving a second aerosol precursor composition from a second source container, the second aerosol precursor composition differing from the first aerosol precursor composition at operation 804. The method may additionally include mixing the first aerosol precursor composition and the second aerosol precursor composition in a mixing container to form a mixed aerosol precursor composition at operation 806. The method may further include dispensing the mixed aerosol precursor composition to an aerosol delivery device.

In some embodiments of the method receiving the first aerosol precursor composition from the first source container at operation 802 may include opening a first source container outlet valve and a mixing container inlet valve. Further, receiving the second aerosol precursor composition from the second source container at operation 804 may include opening a second source container outlet valve and the mixing container inlet valve. Opening the first source container outlet valve and the mixing container inlet valve may include engaging the first source container outlet valve with the mixing container inlet valve. Similarly, opening the second source container outlet valve and the mixing container inlet valve may include engaging the second source container outlet valve with the mixing container inlet valve.

Further, the method may include closing the first source container outlet valve and the mixing container inlet valve during disengagement thereof. Additionally, the method may include closing the second source container outlet valve and the mixing container inlet valve during disengagement thereof. Dispensing the mixed aerosol precursor composition to the aerosol delivery device at operation 808 may include opening a mixing container outlet valve. Further, the method may include closing the mixing container outlet valve during disengagement from the aerosol delivery device.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device filling system, comprising:
   a first source container including an extension at least partially extending out of the first source container and a first aerosol precursor composition contained in the first source container;
   a second source container including an extension at least partially extending out of the second source container and a second aerosol precursor composition differing from the first aerosol precursor composition contained in the second source container;
   a mixing container comprising a mixing container inlet defining a receptacle, the receptacle of the mixing container being arranged to receive the extension of the first source container therein upon engagement of the mixing container and the first source container so as to receive at least a portion of the first aerosol precursor composition in the mixing container, and the receptacle of the mixing container being arranged to receive the extension of the second source container therein upon engagement of the mixing container and the second source container so as to receive at least a portion of the second aerosol precursor composition in the mixing container to form a mixed aerosol precursor composition; and an aerosol delivery device configured to engage the mixing container to receive at least a portion of the mixed aerosol precursor composition.

2. The aerosol precursor composition mixing system of claim 1, wherein at least one of the first source container and the second source container further includes a pressurized propellant.

3. The aerosol precursor composition mixing system of claim 1, wherein at least one of the first source container and the second source container comprises a pump mechanism configured to pump the aerosol precursor composition into the mixing container.

4. The aerosol delivery device filing system of claim 1, wherein the first source container and the second source container respectively define a source container outlet and include a source container outlet valve coupled to the source container outlet.

5. The aerosol delivery device filling system of claim 4, wherein the mixing container defines a mixing container outlet and includes a mixing container inlet valve coupled to the mixing container inlet and a mixing container outlet valve coupled to the mixing container outlet, the source container outlet valve of the first source container and the mixing container inlet valve being configured to engage one another and open during engagement to allow transfer of the aerosol precursor composition from the first source container to the mixing container, the source container outlet valve of the second source container and the mixing container inlet valve being configured to engage one another and open during engagement to allow transfer of the aerosol precursor composition from the second source container to the mixing container, the mixing container outlet valve being configured to open during engagement with the aerosol delivery device.

6. The aerosol delivery device filling system of claim 5, wherein at least one of the source container outlet valve, the mixing container inlet valve, and the mixing container outlet valve comprises a one-way valve.

7. The aerosol precursor composition mixing system of claim 6, wherein the one-way valve comprises a spring configured to bias the one-way valve to a closed configuration.

8. A method for customizing an aerosol precursor composition, the method comprising:

engaging a receptacle defined by a mixing container inlet of a mixing container with an extension of a first source container, the extension of the first source container at least partially extending out of the first source container and into the receptacle of the mixing container during engagement thereof;

receiving at least a portion of a first aerosol precursor composition from the first source container in the mixing container;

engaging the receptacle of the mixing container with an extension of a second source container, the extension of the second source container at least partially extending out of the second source container and into the receptacle of the mixing container during engagement thereof;

receiving at least a portion of a second aerosol precursor composition from the second source container in the mixing container, the second aerosol precursor composition differing from the first aerosol precursor composition;

mixing the first aerosol precursor composition and the second aerosol precursor composition in the mixing container to form a mixed aerosol precursor composition; and dispensing the mixed aerosol precursor composition to an aerosol delivery device.

9. The method of claim 8, wherein receiving the first aerosol precursor composition from the first source container comprises opening a first source container outlet valve and a mixing container inlet valve, and wherein receiving the second aerosol precursor composition from the second source container comprises opening a second source container outlet valve and the mixing container inlet valve.

10. The method of claim 9, wherein opening the first source container outlet valve and the mixing container inlet valve comprises engaging the first source container outlet valve with the mixing container inlet valve, and wherein opening the second source container outlet valve and the mixing container inlet valve comprises engaging the second source container outlet valve with the mixing container inlet valve.

11. The method of claim 10, further comprising closing the first source container outlet valve and the mixing container inlet valve during disengagement thereof; and closing the second source container outlet valve and the mixing container inlet valve during disengagement thereof.

12. The method of claim 8, wherein dispensing the mixed aerosol precursor composition to the aerosol delivery device comprises opening a mixing container outlet valve.

13. The method of claim 12, further comprising closing the mixing container outlet valve during disengagement from the aerosol delivery device.

* * * * *